US009931353B2

(12) United States Patent
Wustman et al.

(10) Patent No.: US 9,931,353 B2
(45) Date of Patent: *Apr. 3, 2018

(54) METHOD FOR TREATING CEREBRAL AMYLOID ANGIOPATHY USING PHARMACOLOGICAL CHAPERONES TO INCREASE THE ACTIVITY OF GANGLIOSIDASES

(71) Applicant: Amicus Therapeutics, Inc., Cranbury, NJ (US)

(72) Inventors: Brandon Alan Wustman, San Diego, CA (US); Kenneth Valenzano, East Brunswick, NJ (US); Robert Boyd, Horsham, PA (US)

(73) Assignee: Amicus Therapeutics, Inc., Cranbury, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/704,445

(22) Filed: May 5, 2015

(65) Prior Publication Data

US 2015/0374733 A1 Dec. 31, 2015

Related U.S. Application Data

(62) Division of application No. 13/501,586, filed as application No. PCT/US2010/052351 on Oct. 12, 2010, now Pat. No. 9,044,437.

(60) Provisional application No. 61/252,799, filed on Oct. 19, 2009.

(51) Int. Cl.
*A61K 31/7008* (2006.01)
*A61K 31/445* (2006.01)
*A61K 38/17* (2006.01)
*A61K 31/426* (2006.01)
*A61K 31/429* (2006.01)

(52) U.S. Cl.
CPC ........ *A61K 31/7008* (2013.01); *A61K 31/426* (2013.01); *A61K 31/429* (2013.01); *A61K 31/445* (2013.01); *A61K 38/1709* (2013.01)

(58) Field of Classification Search
CPC .............. A61K 31/7008; A61K 31/445; A61K 38/1709; A61K 31/426; A61K 31/429
See application file for complete search history.

(56) References Cited

U.S. PATENT DOCUMENTS

| 2005/0031651 A1 | 2/2005 | Gervais et al. |
| 2007/0021381 A1 | 1/2007 | Fan et al. |
| 2007/0066543 A1 | 3/2007 | Mahuran et al. |
| 2008/0009516 A1 | 1/2008 | Wustman |
| 2016/0008383 A1* | 1/2016 | Wustman ............ A61K 31/445 514/315 |

FOREIGN PATENT DOCUMENTS

| WO | WO 2006/133446 | 12/2006 |
| WO | 2007/150064 A2 | 12/2007 |
| WO | WO 2008/134628 | 11/2008 |
| WO | WO 2011/011181 | 1/2011 |

OTHER PUBLICATIONS

Alzheimer's Drug Discovery Foundation Funds Amicus Therapeutics to Advance Pharmalogical Chaperone Technology, Amicus Therapeutics, Inc., retrieved from the Internet http://www.alzdisvoery.org/wp-content/uploads/2010/05/addf-amicus-press-release.pdf May 6, 2012, 2 pages.
International Search Report in PCT/US2010/052351, dated Nov. 25, 2010, 2 pages.
Supplemental European Search Report in EP10825421.0, dated May 14, 2013, 8 pages.
Cataldo, Anne M., et al., Lysosomal hydrolases of different classes are abnormally distributed in brains of patients with Alzheimer disease, *Proc. Natl. Acad. Sci.*, vol. 88 Dec. 1991, 10998-11002.
Hinek, et al., Lysosomal sialidase (muraminidase-1) is targeted to the cell surface in a Multiprotein complex that facilitates elastic fiber assembly, *Journal of Biological Chemistry* vol. 281 No. 6 2005, 3698-3710.
Keilani, Serene, et al., Lysosomal Dysfunction in a Mouse Model of Sandhoff Disease Leads to Accumulation of Ganglioside-Bound Amyloid-B Peptide, *The Journal of Neuroscience* Apr. 11, 2012, 5223-5236.
Knight, E. M., et al., Evidence that small molecule enhancement of B-hexosaminidase activity corrects the behavioral phenotype in Dutch APP E693Q mice through reduction of ganglioside-bound AB, *Molecular Psychiatry* 2014, 1-9.
Koren III, John, et al., Chaperone signalling complexes in Alzheimer's disease, *Journal of Cellular and Molecular Medicine* vol. 13 No. 4 Apr. 2009, 619-630.
Ringe, Dagmar, et al., What are pharmacological chaperones and why are they interesting?, *Journal of Biology* vol. 8 No. 9 2009, 80.
Yerbury, Justin J., et al., Extracellular chaperones modulate the effects of Alzheimer's patient cerebrospinal fluid on Abeta (1-42) toxicity and uptake, *Cell Stress & Chaperones* vol. 15 No. 1 Jan. 2010, 115-121.
Yuzwa, Scott A., et al., A potent mechanism-inspired O-GlcNAcase inhibitor that blocks phosphorylation of tau in vivo, *Nature Chemical Biology*, vol. 4, No. 8 Aug. 2008, 24 pages.
Non-Final Office Action in U.S. Appl. No. 13/501,586, dated Sep. 2, 2014, 11 pages.
Non-Final Office Action in U.S. Appl. No. 13/501,586, dated Feb. 26, 2014, 9 pages.
Yuzwa et al., "A potent mechanism-inspired 0-GlcNAcase inhibitor that blocks phosphorylation of tau in vivo", Nature chemical Biology, Aug. 2008, pp. 483-490, vol. 4, No. 8, Macmillan Publishers Limited, London, United Kingdom.

(Continued)

*Primary Examiner* — Kara R McMillian
(74) *Attorney, Agent, or Firm* — Servilla Whitney LLC

(57) ABSTRACT

The present invention relates to a method for treating an individual having Cerebral Amyloid Angiopathy by using pharmacological chaperones to increase the activity of gangliosidase and/or sialidase enzymes involved in ganglioside catabolism.

6 Claims, 8 Drawing Sheets

(56) References Cited

OTHER PUBLICATIONS

Tropak et al., "High-Throughput Screening for Human Lysosomal beta-N-Acetyl Hexosaminidase Inhibitors Acting as Pharmacological Chaperones", Chemistry & Biology, Feb. 2007, pp. 153-164, vol. 14, No. 2, Elsevier, Amsterdam, Netherlands.

Merck Manual, the 18th edition, Japanese version, Nov. 2005, Amyloidosis: Endocrine and Metabolic Disorders, [online], Retrieved from the interne: URL: http://merckmanual.jp/mmpej/sec12/ch160/ch160a.html.

* cited by examiner

A

B

C

D

METHOD FOR TREATING CEREBRAL AMYLOID ANGIOPATHY USING PHARMACOLOGICAL CHAPERONES TO INCREASE THE ACTIVITY OF GANGLIOSIDASES

CROSS-REFERENCE TO RELATED APPLICATIONS

This application is a divisional of U.S. patent application Ser. No. 13/501,586, which is the National Phase entry of PCT/US2010/052351, filed Oct. 12, 2010, which claims the benefit of U.S. Provisional Application No. 61/252,799, filed Oct. 19, 2009, the contents of which are incorporated by reference herein.

FIELD OF THE INVENTION

The present invention relates to a method for treating an individual having Alzheimer's Disease by using pharmacological chaperones to increase the activity of gangliosidase and/or sialidase enzymes involved in ganglioside catabolism.

BACKGROUND OF THE INVENTION

Alzheimer's Disease is one of the largest socioeconomic healthcare burdens. Alzheimer's disease is characterized by progressive dementia and histopathologically by the presence of neurofibrillary tangles (NFTs) and neuritic (senile) plaques. Plaques consist of a protein called Amyloid (Aβ) and tangles are made up of a protein called Tau.

Amyloid plaques and NFTs are both hallmarks of Alzheimer's disease. Mutations in APP and presenilin lead to early onset forms of Alzheimer's disease, supporting the hypothesis that the processing of APP may also play an important role in the pathogenesis of sporadic AD. Furthermore, the "amyloid hypothesis" predicts that the accumulation of Aβ in some toxic form is harmful to the brain. APP can be processed by α- and β-secretase pathways. To date, most research efforts to develop AD therapies that retard the progression of the disease are focused on inhibition of γ-secretase and β-secretase and the metabolism of APP to form Aβ peptide or activation of α-secretase processing to increase production of the neuroprotective sAPPα peptide while reducing Aβ production. Developing specific β-secretase inhibitors has been difficult, in part because there appears to be a nonlinear relationship between decrease of β-secretase activity in vivo, and a reduction of Aβ peptides in the brain. A further difficulty is the low brain penetration of most inhibitors. γ-secretase inhibitors have been further plagued with severe GI side effects associated with notch inhibition since γ-secretase processes numerous other substrates in addition to APP, including the notch receptor. Additionally, a deficiency of γ-secretase activity has been shown to cause neurodegeneration and may be associated with autosomal-dominant early-onset Alzheimer's disease caused by mutations in presenilin 1 (a component of the γ-secretase complex that contains the active site of the γ-secretase complex).

The majority of efforts aimed at treating Alzheimer's Disease (AD) have focused on reducing the symptoms of AD. In particular, identification of a lower concentration of choline acetyltransferase in affected neurons of the forebrains of AD patients has lead to treatments aimed at inhibiting the hydrolysis of acetylcholine in the synaptic cleft and prolonging the level of acetylcholine at the synapse. Although this strategy has resulted in at least a partial correction of neurotransmitter levels, the therapeutic benefits have been small.

Further, AD is categorized as a tauopathy. Tauopathies are caused by abnormal hyperphosphorylation of tau promoting its aggregation and formation of neurofibrillary tangles (NFTs). Since mutations in tau and APP both cause dementia, one or both may contribute to the disease progression of AD. It is well understood that mutations leading to altered processing of APP cause AD. Currently, there are no approved therapies for slowing the progression of Alzheimer's disease. Thus, there remains a need for more beneficial AD treatments. While most therapies in development are focused on altering APP metabolism (e.g. β-secretase and γ-secretase inhibition) or blocking tau aggregation, the present invention provides a treatment using pharmacological chaperones which bind to one or more gangliosidases and/or sialidases and thereby increase the production of sAPPα and reduce the production of Aβ and hyperphosphorylated tau.

All citations herein are incorporated by reference in their entirety.

SUMMARY OF THE INVENTION

The present invention relates to a method for the treatment of Alzheimer's Disease by administering a pharmacological chaperone which reduces ganglioside levels by increasing the activity of one or more gangliosidase and/or sialidase enzymes involved in the catabolism of certain gangliosides.

In accordance with one embodiment, there is provided a method for the treatment of Alzheimer's Disease in an individual, comprising administering to the individual an effective amount of a pharmacological chaperone. In another embodiment the pharmacological chaperone binds to one or more gangliosidase and/or a sialidase enzymes or glucocerebrosidase. In a further embodiment, the pharmacological chaperone increases mutant and/or wild-type gangliosidase and/or sialidase activity.

In one embodiment, there is provided a method for the treatment of Cerebral Amyloid Angiopathy. In another embodiment, CAA is Familial CAA caused by mutations in APP.

The present invention also relates to a method for the treatment of a condition resulting from the pathological aggregation of tau protein, including, diseases such as Alzheimer's Disease, Progressive supranuclear palsy, Corticobasal degenerations and Frontotemporal lobar degeneration, by administering a pharmacological chaperone which increases the activity of one or more gangliosidases and/or sialidase enzymes involved in the catabolism of certain gangliosides or increases the activity of glucocerebrosidase.

The present invention provides compounds, known as pharmacological chaperones, and methods for using these compounds to prevent and/or treat Alzheimer's disease in a patient at risk for developing or diagnosed with the same, which includes administering to the patient in need thereof a compound selected from Formulas I, II and III as set forth herein, as well as those specified in the Examples.

In one embodiment, the pharmacological chaperones is 2-acetamido-1,2-dideoxynojirimycin or a pharmaceutically acceptable salt, solvent, or prodrug thereof. In one embodiment, the pharmacological chaperone is 5-(fluoromethyl)piperdine-3,4-diol or a pharmaceutically acceptable salt, solvate, or prodrug thereof. In one embodiment, the pharmacological chaperone comprises (3R,4R,5R)-5-(fluoromethyl)piperdine-3,4-diol or a pharmaceutically acceptable salt, solvate, or prodrug thereof. In one embodiment, the pharmacological chaperone comprises (3R,4R,5R)-5-(fluoromethyl)piperdine-3,4-diol hydrochloride. In one embodiment, the method comprises administering 5-(chloromethyl)piperdine-3,4-diol or a pharmaceutically acceptable salt, solvate, or prodrug thereof. In one embodiment, the method comprises administering (3R,4R,5S)-5-(chloromethyl)piperdine-3,4-diol or a pharmaceutically acceptable salt, solvate, or prodrug thereof. In one embodiment, the method comprises administering (3R,4R,5S)-5-(chloromethyl)piperdine-3,4-diol.

DETAILED DESCRIPTION OF THE INVENTION

Figure 1:
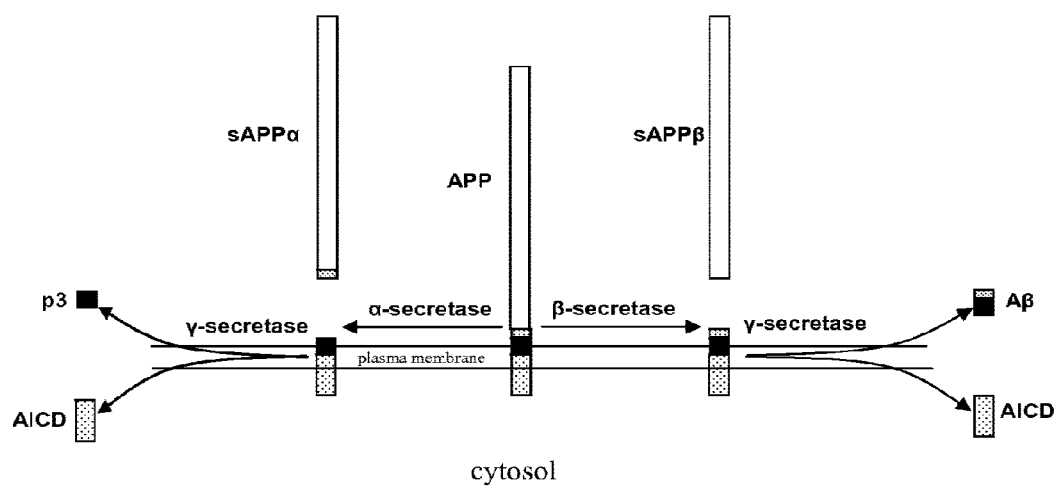
FIG. 1 shows a schematic for APP processing.

Aβ is a hydrophobic 38- to 43-amino acid peptide, found in all biological fluids, and derived from the enzymatic cleavage of a larger type I membrane protein, the amyloid precursor protein (APP). See FIG. 1, which depicts APP processing. Linkage studies of familial AD patients identified a number of mutations in two genes, APP and presenilin, associated with aberrant metabolism of APP and an increased production of aggregating forms of Aβ. It is thought that Aβ forms toxic oligomers which may play a significant role in the pathology of Alzheimer's disease (Shankar et al., 2008).

Gangliosides promote the generation of neurotoxic forms of Aβ in the brain (i.e. oligomers). Gangliosides are sialic acid-containing glycosphingolipids that are found in the outer leaflet of cell membranes, and are particularly abundant on the cell surface of neurons. Gangliosides are known to exist in clusters and to form microdomains on the surface of the plasma membrane. This specific localization of gangliosides enables them to interact with a variety of bioeffectors, including glycoproteins, peptide hormones, and growth factors. Furthermore, gangliosides (e.g. GM1 ganglioside) can promote cell differentiation, prevent loss of neurogenesis, and play a neuroprotective role in in vitro and in vivo models of neuronal injury.

Gangliosides are most abundant in the nervous system and are involved in a variety of functions, including mediation of signal transduction, cell adhesion and cell differentiation. While over 200 gangliosides have been identified, the majority of gangliosides in neurons are catabolized by one or more gangliosidases and/or sialidases.

The products of α-secretase activity, soluble APPα (sAPPα), and β-secretase activity, soluble APPβ (sAPPβ), differ by the inclusion in sAPPα of the first 16 residues of Aβ. Since cleavage of APP by α-secretase bisects the Aβ domain, none of the products of the reaction can give rise to amyloid. Thus, activation of or upregulation of α-secretase activity is hypothesized to prevent or reduce the formation of toxic Aβ oligomers and amyloid plaques, while increasing the shedding of neurotrophic and neuroprotective sAPPα. Interestingly, inhibiting the synthesis of glycosphingolipids and gangliosides has been shown to activate the shedding of sAPPα (Sawamura et al., 2004).

Mutations in APP also cause familial Alzheimer's disease and/or Cerebral Amyloid Angiopathy (CAA). The gangliosides GM2, GM3 and GD3 may modulate regional Aβ deposition since they are expressed in an area-specific manner in the brain. (Yamamoto et al., 2006) have shown that assembly of hereditary variant Dutch- and Italian-type Aβs, and Flemish-type Aβ was accelerated by GM3 ganglioside and GD3 ganglioside, respectively. Notably, cerebrovascular smooth muscle cells, which compose the cerebral vessel wall where the Dutch- and Italian-type Aβs deposit, exclusively express GM2 and GM3 (Yamamoto et al., 2006). Thus, the assembly of hereditary Aβ variants may be accelerated by local environmental factors, such as the presence of particular gangliosides in the brain.

The present invention provides compounds, known as pharmacological chaperones, and methods for using these compounds to prevent and/or treat Alzheimer's disease in a patient at risk for developing or diagnosed with the same, which includes administering to the patient in need thereof an effective amount of a pharmacological chaperone including compounds of formula I:

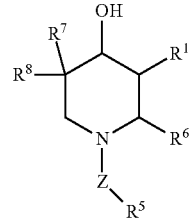

Formula I wherein:
$R^1$ is $C(R^2)(R^3)(R^4)$;
$R^2$ is hydrogen, —OH or halogen;
$R^3$ is hydrogen, —OH, halogen or $C_{1-8}$ alkyl;
$R^4$ is halogen, $C_{1-8}$ alkyl, substituted $C_{1-8}$ alkyl, aryl, substituted aryl, alkylcycloalkyl or substituted alkylcycloalkyl;
$R^3$ and $R^4$ may join with the carbon to which they are attached to form a cycloalkyl ring, which may be optionally substituted, preferably with halogen and more preferably with one or more fluorine atoms;
$R^6$ is hydrogen, $C_{1-8}$ alkyl, substituted $C_{1-8}$ alkyl, arylalkyl, substituted arylalkyl, alkylaryl, or substituted alkylaryl;

Z is optional, when present Z is —(CH$_2$)$_{1-8}$—, —C(=O)—, —S(=O)$_2$NH—, —S(=O)$_2$—, —C(=S)NH—, —S(=O)$_2$—CH$_3$, C(=O)—NH—, —S(=O)$_2$—NR$^9$R$^{10}$, —C(=O)C$_{1-8}$ alkyl or —C(=O)CH(NH$_2$)CH$_3$;

R$^9$ is hydrogen, C$_{1-8}$ alkyl or substituted C$_{1-8}$ alkyl;

R$^{10}$ is hydrogen, C$_{1-8}$ alkyl or substituted C$_{1-8}$ alkyl;

R$^5$ is hydrogen, C$_{1-8}$ alkyl, substituted C$_{1-8}$ alkyl, aryl, substituted aryl, C$_{1-8}$ alkenyl, substituted C$_{1-8}$ alkenyl, arylalkyl, substituted arylalkyl, alkylaryl, substituted alkylaryl, aminoarylalkyl or substituted aminoarylalkyl;

R$^7$ is —OH or halogen; and

R$^8$ is hydrogen, halogen or C$_{1-8}$ alkyl, provided that R$^2$ and R$^3$ cannot both be hydrogen when R$^4$ is a halogen, Z is not present, R$^7$ is —OH, R$^5$, R$^6$ and R$^8$ are hydrogen.

The present invention provides compounds, known as pharmacological chaperones, and methods for using these compounds to prevent and/or treat Alzheimer's disease in a patient at risk for developing or diagnosed with the same, which includes administering to the patient in need thereof an effective amount of a pharmacological chaperone including compounds of formula II:

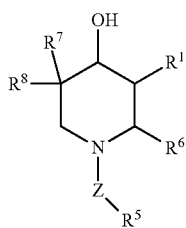

Formula II wherein:
R$^1$ is C(R$^2$)(R$^3$)(R$^4$);
R$^2$ is hydrogen, —OH or halogen;
R$^3$ is hydrogen, —OH, halogen or —CH$_3$;
R$^4$ is halogen, —CH$_3$, phenyl, fluorophenyl, methylphenyl, cyclohexylmethyl, wherein when R$^4$ is a halogen, both R$^2$ and R$^3$ cannot be hydrogen;
R$^3$ and R$^4$ may join with the carbon to which they are attached to form a cycloalkyl ring, which may be optionally substituted with one or more halogen atoms;
R$^6$ is hydrogen, phenylalkyl or substituted phenylalkyl;
Z is optional, when present Z is —(CH$_2$)—, —C(=O)—, —S(=O)$_2$NH—, —S(=O)$_2$—, —S(=O)$_2$—CH$_3$, C(=O)—NH—, —S(=O)$_2$NR$^9$R$^{10}$, —C(=S)—NH— or —C(=O)$_2$—CH$_3$,
R$^9$ is hydrogen or CH$_3$;
R$^{10}$ is hydrogen or CH$_3$;
R$^5$ is hydrogen or aminophenylalkyl;
R$^7$ is —OH or halogen; and
R$^8$ is hydrogen, halogen or —CH$_3$,
provided that R$^2$ and R$^3$ cannot both be hydrogen when R$^4$ is halogen, Z is not present, R$^7$ is —OH, R$^5$, R$^6$ and R$^8$ are hydrogen.

The present invention further provides compounds, known as pharmacological chaperones, and methods for using these compounds to prevent and/or treat Alzheimer's disease in a patient at risk for developing or diagnosed with the same, which includes administering to the patient in need thereof an effective amount of a pharmacological chaperone including compounds of formula III:

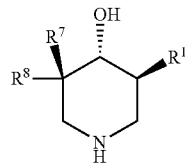

Formula III wherein:
R$^1$ is C(R$^2$)(R$^3$)(R$^4$);
R$^2$ is hydrogen, —OH or halogen;
R$^3$ is hydrogen, —OH, halogen or —CH$_3$;
R$^4$ is halogen, —CH$_3$, phenyl, fluorophenyl, methylphenyl, cyclohexylmethyl, wherein when R$^4$ is a halogen, both R$^2$ and R$^3$ cannot be hydrogen;
R$^3$ and R$^4$ may join with the carbon to which they are attached to form a cycloalkyl ring, which may be optionally substituted with one or more halogen atoms;
R$^7$ is —OH or halogen; and
R$^8$ is hydrogen, halogen or —CH$_3$,
provided that R$^2$ and R$^3$ cannot both be hydrogen when R$^4$ is a halogen, R$^7$ is —OH and R$^6$ and R$^8$ are hydrogen.

It is understood by a person of ordinary skill in the art that R$^2$, R$^3$ and R$^4$ will not be selected such that an unstable molecule will result.

Listed below are definitions of various terms used to describe this invention. These definitions apply to the terms as they are used throughout this specification, unless otherwise limited in specific instances, either individually or as part of a larger group.

The term "alkyl" refers to straight or branched chain unsubstituted hydrocarbon groups of 1 to 20 carbon atoms, preferably 1 to 8 carbon atoms, more preferably 1 to 6 carbon atoms. The expression "lower alkyl" refers to unsubstituted alkyl groups of 1 to 4 carbon atoms.

The term "substituted alkyl" refers to an alkyl group substituted by, for example, one to four substituents, such as, halo, hydroxy, alkoxy, oxo, alkanoyl, aryloxy, alkanoyloxy, amino, alkylamino, arylamino, aralkylamino, disubstituted amines in which the 2 amino substituents are selected from alkyl, aryl or aralkyl; alkanoylamino, aroylamino, aralkanoylamino, substituted alkanoylamino, substituted arylamino, substituted aralkanoylamino, thiol, alkylthio, arylthio, aralkylthio, alkylthiono, arylthiono, aralkylthiono, alkylsulfonyl, arylsulfonyl, aralkylsulfonyl, sulfonamido, e.g. SO$_2$NH$_2$, substituted sulfonamido, nitro, cyano, carboxy, carbamyl, e.g. CONH$_2$, substituted carbamyl e.g. CONHalkyl, CONHaryl, CONHaralkyl or cases where there are two substituents on the nitrogen selected from alkyl, aryl or aralkyl; alkoxycarbonyl, aryl, substituted aryl, guanidino and heterocyclos, such as, indolyl, imidazolyl, furyl, thienyl, thiazolyl, pyrrolidyl, pyridyl, pyrimidyl and the like. Where noted above where the substituent is further substituted it will be with alkyl, alkoxy, aryl or aralkyl.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "aralkyl" refers to an aryl group bonded directly through an alkyl group, such as benzyl. Similarly, the term "alkylaryl" refers to an alkyl group bonded directly through an aryl group, such as methylbenzyl.

The term "substituted aryl" refers to an aryl group substituted by, for example, one to four substituents such as alkyl, substituted alkyl, halo, trifluoromethoxy, trifluoromethyl, hydroxy, alkoxy, alkanoyl, alkanoyloxy, amino, alkylamino, aralkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, aryloxy and the like. The substituent may be further substituted by hydroxy, alkyl, alkoxy, aryl, substituted aryl, substituted alkyl or aralkyl. In some embodiments, the substituted aryl is a phenylalkyl or a substituted phenylalkyl. In some embodiments, the substituted phenylalkyl is preferably substituted with a halogen, alkoxy or alkyl.

The term "heteroaryl" refers to an optionally substituted, aromatic group for example, which is a 4 to 7 membered monocyclic, 7 to 11 membered bicyclic, or 10 to 15 membered tricyclic ring system, which has at least one heteroatom and at least one carbon atom-containing ring, for example, pyridine, tetrazole, indazole.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "substituted alkenyl" refers to an alkenyl group substituted by, for example, one to two substituents, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino, indolyl, imidazolyl, furyl, thienyl, thiazolyl, pyrrolidyl, pyridyl, pyrimidyl and the like.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

The term "substituted alkynyl" refers to an alkynyl group substituted by, for example, a substituent, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclo, e.g. imidazolyl, furyl, thienyl, thiazolyl, pyrrolidyl, pyridyl, pyrimidyl and the like.

The term "cycloalkyl" refers to an optionally substituted, saturated cyclic hydrocarbon ring systems, preferably containing 1 to 3 rings and 3 to 7 carbons per ring which may be further fused with an unsaturated C3-C7 carbocylic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

The terms "heterocycle", "heterocyclic" and "heterocyclo" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxopyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1, 1-dioxothienyl, dioxanyl, isothiazolidinyl, thietanyl, thiiranyl, triazinyl, and triazolyl, and the like.

Exemplary bicyclic hetrocyclic groups include 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary substituents include one or more alkyl or aralkyl groups as described above or one or more groups described above as alkyl substituents.

Also included are smaller heterocyclos, such as, epoxides and aziridines.

The term "heteroatoms" shall include oxygen, sulfur and nitrogen.

The compounds of formulas I, II and III may form salts which are also within the scope of this invention. Pharmaceutically acceptable (i.e. non-toxic, physiologically acceptable) salts are preferred, although other salts are also useful, e.g., in isolating or purifying the compounds of this invention.

The invention is directed to a method for the treatment of Alzheimer's Disease in an individual by administering to the individual an effective amount of a pharmacological chaperone. Many pharmacological chaperones may be used for the treatment of Alzheimer's Disease, including, but not limited to those described in Tables 1 or 2 or any variants derivatives or analogs thereof.

The present invention is also directed to treating individuals deficient in an enzyme activity associated with Alzheimer's disease, including, but not limited to the enzyme activity of β-hexosaminidase A, β-hexosaminidase B, β-hexosaminidase S, neuraminidase-1, neuraminidase-2, neuraminidase-3, neuraminidase-4 and glucocerebrosidase.

In one embodiment of the invention, the pharmacological chaperone binds to one or more gangliosidase and/or sialidase enzymes. The pharmacological chaperone may bind to a gangliosidase and/or sialidase enzyme, or glucocerebrosidase, associated with Alzheimer's Disease or associated with the hallmarks of Alzheimer's Disease or any disease associated with the accumulation of the Tau protein. Gangliosidases may include, for example, β-hexosaminidase A, β-hexosaminidase B, neuraminidase-2, neuraminidase-3, neuraminidase-4 and glucocerebrosidase or any other gangliosidase associated with Alzheimer's disease or any disease associated with the accumulation of the tau protein. Sialidases may include neuraminidase-1 and neuraminidase-4 or any other sialidase associated with Alzheimer's Disease or any disease associated with the accumulation of the tau protein.

In another embodiment, the pharmacological chaperone increases trafficking of the gangliosidase and/or sialidase from the endoplasmic reticulum (ER) to the enzymes final location in a cell where it performs its enzymatic function. In the cases of neuraminidase 1, β-hexosaminidase A and β-hexosaminidase B, pharmacological chaperones increases trafficking of the enzymes from the ER to the lysosome. In the case of neuraminidase 2, pharmacological chaperones increase trafficking of the enzymes from the ER to the cytosol. In the case of neuraminidase 3, pharmacological chaperones increase trafficking of the enzyme from the ER to the endosomes and plasma membrane. In the case of neuraminidase 4, pharmacological chaperones increase trafficking of the enzyme from the ER to the lysosomal and mitochondria. In the case of glucocerebrosidase, the pharmacological chaperone increases trafficking of the enzyme from the ER to the lysosome. The pharmacological chaperone may increase mutant and/or wild-type gangliosidase and/or sialidase activity. Further, the gangliosidase or sialidase may catabolize one or more gangliosides. The activity of the enzyme may be increased by up to 5%. The activity of the enzyme may also be increased by up to 10%, 20%, 40%, more than 50%, nearly 100% or even more than 100%.

In one embodiment, the enzyme is β-hexosaminidase A and the ganglioside to be catabolized is GM2. In another embodiment, the enzyme is β-hexosaminidase B and the gangliosides to be catabolized are GA2 and GM2. In another embodiment, the enzyme is β-hexaminidase S and the products to be catabolized are sulfated gangliosides, sulfated glycosphingolipids, sulfated glycosyl amino glycans, sulfated oligosaccharides and dermatan sulfate. In another embodiment, the enzymes are neuraminidase 2, neuraminidase 3 and neuraminidase 4 and the ganglio sides to be catabolized are sialic acid containing gangliosides. In another embodiment, the enzyme is neuraminidase 1 and the substrate to be catabolized is glycoproteins and oligosaccharides with terminal sialic acid. In another embodiment, the enzyme is glucocerebrosidase and the glycosphingolipid to be catabolized is glucosylceramide. Glucocerebroside is a precursor of a ganglioside in the context of ganglioside synthesis and a product of a ganglioside in the context of ganglioside catabolism. Glucocerebroside is the first step in the synthesis of all glycosphingolipids, including gangliosides and it is the final step in catabolism of the gangliosides and other glycosphingolipids.

In one aspect of the invention, the pharmacological chaperone is N-acetylglucosamine thiazoline (NGT). In another aspect the pharmacological chaperone is N-butyl-deoxygalactonojirimycin (NB-DGJ). In another aspect the pharmacological chaperone is 4-epi-isofagomine (4-epi-IFG). In another aspect the pharmacological chaperone is 2-acetamido-2-deoxynojirimycin (AdDNJ). In another aspect, the pharmacological chaperone is Zanamivir, 5-(acetylamino)-4-[(aminoiminomethyl)-amino]-2,6-anhydro-3,4,5-trideoxy-D-glycero-D-galacto-non-2-enonic acid.

In one aspect of the invention, the pharmacological chaperone NB-DGJ also functions to reduce the synthesis of gangliosides by inhibiting glucosylceramide synthase, the enzyme which catalyzes the first step in the synthesis of glycosphingolipids and gangliosides. NB-DGJ is a pharmacological chaperone that can also function as an SRT. Other pharmacological chaperones also have this dual function.

In another aspect of the invention, a pharmacological chaperone may be combined with N-butyldeoxynojirimycin (NB-DNJ), an inhibitor of glucosylceramide synthase. The pharmacological chaperone and NB-DNJ may be dosed simultaneously daily, one time per week, twice per week, three times per week, four days per week, five days per week, or even less or more frequently or as needed. One or more pharmacological chaperones and NB-DNJ may also be dosed separately or simultaneously and each dosed one time per week, twice per week, three times per week, or four or more times per week or as needed.

Many different pharmacological chaperones may be used to treat Alzheimer's Disease, including, but not limited to, those listed in Tables 1 and 2. Additional pharmacological chaperones that increase the activity of one or more gangliosidase or sialidase enzymes may be found in Tropak et al., The Journal of Biol. Chem. 279 (14), 13478-13487 (2004), as well as the chemical structures for many of the compounds listed in Tables 1 and 2.

TABLE 1

| Target Enzyme | Pharmacological Chaperone |
|---|---|
| Neuraminidase 1: | n-Butyl 2-deoxy-2,3-dehydro-N-acetylneuraminic acid; (n-Butyl DANA) (NB-DANA) |
| | Phenyl 2-deoxy-2,3-dehydro-N-acetylneuraminic acid; (Phenyl DANA) |
| | Propyl 2-deoxy-2,3-dehydro-N-acetylneuraminic acid; (Propyl DANA) |
| | Methyl 2-deoxy-2,3-dehydro-N-acetylneuraminic acid; (Methyl DANA) |
| | 2-deoxy-2,3-dehydro-N-acetylneuraminic acid; (DANA) |
| | Siastatin B |
| | Lithocholic acid |
| | Lithocholic acid derivatives |
| | Siastatin B analogs 14, 15 and 16 |
| Neuraminidase 2: | Zanamivir (5-(acetylamino)-4-[(aminoiminomethyl)-amino]-2,6-anhydro-3,4,5-trideoxy-D-glycero-D-galacto-non-2-enonic acid) |
| | Lithocholic acid |
| | Lithocholic acid derivatives |
| | 2-deoxy-2,3-dehydro-N-acetylneuraminic acid; (DANA) |
| | Siastatin B and Sistatin B analogs 14, 15 and 16 |
| Neuraminidase 3: | Zanamivir (5-(acetylamino)-4-[(aminoiminomethyl)-amino]-2,6-anhydro-3,4,5-trideoxy-D-glycero-D-galacto-non-2-enonic acid) |
| | Lithocholic acid |
| | Lithocholic acid derivatives |
| | 2-deoxy-2,3-dehydro-N-acetylneuraminic acid; (DANA) |
| | Siastatin B and Sistatin B analogs 14, 15 and 16 |
| Neuraminidase 4: | 2-deoxy-2,3-dehydro-N-acetylneuraminic acid; (DANA) |
| | Siastatin B and Sistatin B analogs 14, 15 and 16 |
| Beta-Hexosaminidase A and B: | N-acetyl-glucosamine-thiazoline; (NGT) |
| | 2-acetamido-1,2-dideoxynojirimycin; (AdDNJ) |
| | 2-acetamido-2-deoxynojirimycin; (ADNJ) |
| | 6-acetamido-6-deoxycastanospermine |
| | Pyrimethamine |
| | Inhibitors identified by HTS screen in: Chemistry & Biology 2007 14,153-164 |
| | 2-acetamido-1,4-imino-1,2,4-trideoxy-L-arabinitol; (LABNAc) |
| | N-benzyl 2-acetamido-1,4-imino-1,2,4-trideoxy-L-arabinitol; (NBn-LABNAc) |

TABLE 1-continued

| Target Enzyme | Pharmacological Chaperone |
|---|---|
| | N-butyl 2-acetamido-1,4-imino-1,2,4-trideoxy-L-arabinitol; (NBu-LABNAc) DABNAc |
| | (2R,3R,4S,5R)-2-Acetamido-3,4-dihydroxy-5-hydroxy-methyl-piperidinium hydrochloride; (GalNAc-isofagomine HCl) |
| | Galactose O-(2-acetamido-2-deoxy-d-glucopyranosylidene)-amino-N-phenylcarbamate; (Gal-PUGNAc) |
| | Derivatives of Gal-PUGNAc as described for PUGNAc |
| | NAG-thiazoline (and its derivatives) |
| | PUGNAc (and its derivatives) |
| | 6-Acetamido-2,6-dideoxy-2-C-hydroxymethyl-Dgluco-δ-lactam |
| | 1-N-imino-2 acetamidomethyl derivative 5 |
| | 2-acetamido-2-deoxy-d-glucono-d-lactam |
| | 2-acetamido-2-deoxy-d-glucono-deoxynojirimycin |
| | 3-hydroxypipecolic acid derivatives |
| | 3,4,5-trihydroxypipecolic acid derivatives |
| | Imidazopyridines 14 and 15 |
| | (3R,4R,5R,6R)-Tetrahydroxyazepane |
| | NAc-1-Cp |
| | Nac-1-(CH$_3$)$_2$ |
| | (5R,6S,7S,8S)-8-Acetamido-5,6,7,8-tetrahydro-5-(hydroxymethyl)-imidazol[1,2-a] pyridine-6,7-triol |
| | 2-Acetoamido-1,2,5-trideoxy-1,5-imino-D-glucitol |
| | (2R,3R,4S,5R)-2-Acetamido-5-aminomethyl-3,4-dihydroxy-piperidine |
| | (2R,3R,4S,5R)-2-Acetamido-5-hydroxymethyl-3,4-dihydroxy-piperidine |
| Glucocerebrosidase (Gcase): | isofagomine |
| | N-Nonyl-DNJ |
| | 6-Benzyl Isofagomine Hydrochloride |
| | 5-epi-Isofagomine |
| | Glucoimidazole hydrochloride |
| | N-Octyl-β-Valienamine |
| | 6-(4-fluoroBenzyl) Isofagomine Hydrochloride |
| | (3R,4R,5R,6S)-6-(2,4-difluorobenzyl)-5-(hydroxymethyl)piperidine-3,4-diol hydrochloride |
| | 3-Methoxy-IFG hydrochloride |
| | N-Propyl IFG |
| | N-Heptyl IFG |
| | N-(piperidin-4-ylmethyl) IFG |
| | N-(2-methoxyethyl) IFG |
| | N-(2-methylbenzyl) IFG Hydrochloride |
| | N-(3-methylbenzyl) IFG hydrochloride |
| | N-((tetrahydro-2H-pyran-4-yl)methyl) IFG |
| | N-(thiophen-2-ylmethyl) IFG |
| | N-(pyridin-4-ylmethyl) IFG |
| | N-Cyclopentylmethyl IFG |
| | N-(5-methylpentyl) IFG |
| | N-(4-aminobenzyl) IFG |
| | N-phenethyl IFG |
| | N-(4-nitrobenzyl) IFG |
| | N-(4-methoxybenzyl) IFG |
| | N-Cyclohexyl IFG |
| | (3S,4R,5R)-3-fluoro-5-(hydroxymethyl)piperidin-4-ol hydrochloride |
| | (3R,4R,5R)-1-(2-cyclohexylethyl)-5-(hydroxymethyl)piperidine-3,4-diol |
| | (3R,4R,5R)-5-(hydroxymethyl)-1-(2-nitrobenzyl)piperidine-3,4-diol |
| | (3R,4R,5R)-1-(3-aminobenzyl)-5-(hydroxymethyl)piperidine-3,4-diol |
| | (3R,4R,5R)-5-(hydroxymethyl)-1-(3-nitrobenzyl)piperidine-3,4-diol |
| | (S)-2-amino-1-((3R,4R,5R)-3,4-dihydroxy-5-(hydroxymethyl)piperidin-1-yl)-4-methylpentan-1-one |
| | (R)-2-amino-1-((3R,4R,5R)-3,4-dihydroxy-5-(hydroxymethyl)piperidin-1-yl)-4-methylpentan-1-one |
| | (3R,4R,5S)-5-(fluoromethyl)piperidine-3,4-diol hydrochloride |
| | (3R,4R,5R)-5-(hydroxymethyl)-1-(3-methylbut-2-enyl)piperidine-3,4-diol |
| | (3R,4R,5R)-1-((E)-3,7-dimethylocta-2,6-dienyl)-3,4-dihydroxy-5-(hydroxymethyl)piperidinium chloride |
| | (3R,4R,5R)-3,4-dihydroxy-5-(hydroxymethyl)-N-propylpiperidine-1-carboxamide |
| | 1-((3R,4R,5R)-3,4-dihydroxy-5-(hydroxymethyl)piperidin-1-yl)pentan-1-one |
| | (3R,4R,5S)-5-(difluoromethyl)piperidine-3,4-diol |
| | (3R,4R,5S)-5-benzylpiperidine-3,4-diol |
| | (3R,4R,5S)-5-(1-hydroxyethyl)piperidine-3,4-diol |
| | (3R,4R,5S)-5-(1-fluoroethyl)piperidine-3,4-diol |
| | (3R,4R,5S)-5-ethylpiperidine-3,4-diol |
| | (3R,4R,5S)-5-isopropylpiperidine-3,4-diol |
| | (3R,4R,5S)-5-(2-hydroxypropan-2-yl)piperidine-3,4-diol |
| | (4R,5R)-3,3-difluoro-5-(hydroxymethyl)piperidin-4-ol |
| | (4R,5R)-5-(hydroxymethyl)-3-methylpiperidine-3,4-diol |
| | (3R,4R,5S)-5-(1,1-difluoroethyl)piperidine-3,4-diol |
| | (3R,4R,5S)-5-(trifluoromethyl)piperidine-3,4-diol |
| | (3R,4R,5S)-5-(2,2-difluoroethyl)piperidine-3,4-diol |
| | (3R,4R,5S)-5-(2-fluoroethyl)piperidine-3,4-diol |
| | (3R,4R,5S)-5-cyclopropylpiperidine-3,4-diol |
| | (3R,4R,5S)-5-(2,2-difluorocyclopropyl)piperidine-3,4-diol |
| | (3R,4R,5S,6S)-6-ethyl-5-(fluoromethyl)piperidine-3,4-diol |
| | (3R,4R,5S,6R)-6-ethyl-5-(fluoromethyl)piperidine-3,4-diol |
| | (3R,4R,5S,6S)-5-(difluoromethyl)-6-ethylpiperidine-3,4-diol |
| | (3R,4R,5S,6R)-5-(difluoromethyl)-6-ethylpiperidine-3,4-diol |
| | (3R,4R,5S)-1-benzyl-5-(difluoromethyl)piperidine-3,4-diol |
| | (3R,4R,5R)-5-((S)-hydroxy(phenyl)methyl)piperidine-3,4-diol |
| | (3R,4R,5S)-1-butyl-5-(difluoromethyl)piperidine-3,4-diol |
| | (3R,4R,5S)-1-allyl-5-(difluoromethyl)piperidine-3,4-diol |
| | 1-((3S,4R,5R)-3-(difluoromethyl)-4,5-dihydroxypiperidin-1-yl)pentan-1-one |
| | (3R,4R,5S)-5-(difluoromethyl)-1-(3-methoxybenzyl)piperidine-3,4-diol |
| | (3R,4R,5S)-5-(difluoromethyl)-1-(4-methylbenzyl)piperidine-3,4-diol |
| | (3R,4R,5S)-5-(difluoromethyl)-1-(methylsulfonyl)piperidine-3,4-diol |
| | (3R,4R,5S)-5-(difluoromethyl)-1-(4-fluorobenzyl)piperidine-3,4-diol |
| | (3R,4R,5R)-5-((4-fluorophenyl)(hydroxy)methyl)piperidine-3,4-diol |
| | (3S,4R,5R)-3-(difluoromethyl)-4,5-dihydroxy-N-propylpiperidine-1-carboxamide |
| | (3R,4R,5S)-5-(difluoromethyl)-1-tosylpiperidine-3,4-diol |

TABLE 1-continued

| Target Enzyme | Pharmacological Chaperone |
|---|---|
| | (3R,4R,5S)-5-(4-methylbenzyl)piperidine-3,4-diol |
| | (3S,4R,5R)-3-(difluoromethyl)-4,5-dihydroxy-N-phenylpiperidine-1-carboxamide |
| | (3S,4R,5R)-3-(difluoromethyl)-4,5-dihydroxy-N-phenylpiperidine-1-carbothioamide |
| | (3S,4R,5R)—N-butyl-3-(difluoromethyl)-4,5-dihydroxypiperidine-1-carboxamide |
| | (3S,4R,5R)—N-butyl-3-(difluoromethyl)-4,5-dihydroxypiperidine-1-carbothioamide |
| | (3S,4R,5R)-3-(difluoromethyl)-4,5-dihydroxy-N,N-dimethylpiperidine-1-sulfonamide |
| | (3R,4R,5S)-5-(2-cyclohexyl-1-hydroxyethyl)piperidine-3,4-diol |
| | (3R,4R,5S)-5-(2-cyclohexyl-1-fluoroethyl)piperidine-3,4-diol |
| | (3R,4R,5S)-5-(4-fluorobenzyl)piperidine-3,4-diol |
| | (3R,4R,5R)-5-((3,5-difluorophenyl)(hydroxy)methyl)piperidine-3,4-diol |
| | (3R,4R,5S)-5-((3,5-difluorophenyl)fluoromethyl)piperidine-3,4-diol |
| | 1-((3S,4R,5R)-3-(difluoromethyl)-4,5-dihydroxypiperidin-1-yl)ethanone |
| | ((3S,4R,5R)-3-(difluoromethyl)-4,5-dihydroxypiperidin-1-yl)(phenyl)methanone |

TABLE 2

| Structure | Name |
|---|---|
| 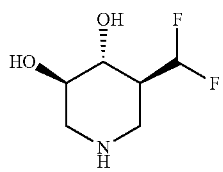 [SMILES: O[C@H]1[C@H](O)CNC[C@@H]1C(F)F] | (3R,4R,5S)-5-(difluoromethyl)piperidine-3,4-diol |
| 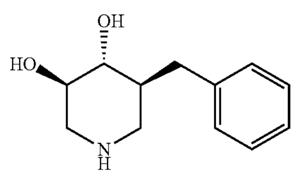 [SMILES: O[C@@H]1[C@@H](Cc2ccccc2)CNC[C@H]1O] | (3R,4R,5S)-5-benzylpiperidine-3,4-diol |
| 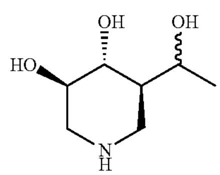 | (3R,4R,5R)-5-(1-hydroxyethyl)piperidine-3,4-diol |
| 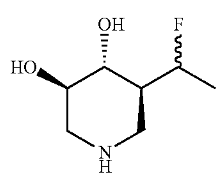 | (3R,4R,5S)-5-(1-fluoroethyl)piperidine-3,4-diol |
| 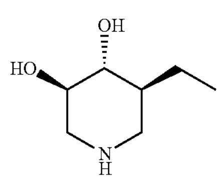 | (3R,4R,5S)-5-ethylpiperidine-3,4-diol |
| 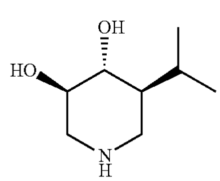 | (3R,4R,5S)-5-isopropylpiperidine-3,4-diol |

TABLE 2-continued

| Structure | Name |
|---|---|
| piperidine with OH, OH, HO, and C(CH3)2OH substituents | (3R,4R,5S)-5-(2-hydroxypropan-2-yl)piperidine-3,4-diol |
| piperidine with OH, OH, F, F substituents | (4R,5R)-3,3-difluoro-5-(hydroxymethyl)piperidin-4-ol |
| piperidine with OH, OH, HO, CH3, CH2OH | (4R,5R)-5-(hydroxymethyl)-3-methylpiperidine-3,4-diol |
| piperidine with OH, OH, HO, C(CH3)F2 | (3R,4R,5S)-5-(1,1-difluoroethyl)piperidine-3,4-diol |
| piperidine with OH, OH, HO, CF3 | (3R,4R,5S)-5-(trifluoromethyl)piperidine-3,4-diol |
| piperidine with OH, OH, HO, CH2CHF2 | (3R,4R,5S)-5-(2,2-difluoroethyl)piperidine-3,4-diol |
| piperidine with OH, OH, HO, CH2CH2F | (3R,4R,5S)-5-(2-fluoroethyl)piperidine-3,4-diol |
| piperidine with OH, OH, HO, cyclopropyl | (3R,4R,5S)-5-cyclopropylpiperidine-3,4-diol |
| piperidine with OH, OH, HO, difluorocyclopropyl | (3R,4R,5S)-5-(2,2-difluorocyclopropyl)piperidine-3,4-diol |

TABLE 2-continued

| Structure | Name |
|---|---|
| (structure) | (3R,4R,5S,6S)-6-ethyl-5-(fluoromethyl)piperidine-3,4-diol |
| (structure) | (3R,4R,5S,6R)-6-ethyl-5-(fluoromethyl)piperidine-3,4-diol |
| (structure) | (3R,4R,5S,6S)-5-(difluoromethyl)-6-ethylpiperidine-3,4-diol |
| (structure) | (3R,4R,5S,6R)-5-(difluoromethyl)-6-ethylpiperidine-3,4-diol |
| (structure) | (3R,4R,5S)-1-benzyl-5-(difluoromethyl)piperidine-3,4-diol |
| (structure) | (3R,4R,5R)-5-((S)-hydroxy(phenyl)methyl)piperidine-3,4-diol |
| (structure) | (3R,4R,5S)-1-butyl-5-(difluoromethyl)piperidine-3,4-diol |

TABLE 2-continued
| 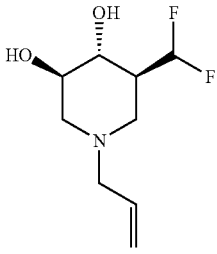 | (3R,4R,5S)-1-allyl-5-(difluoromethyl)piperidine-3,4-diol |
| 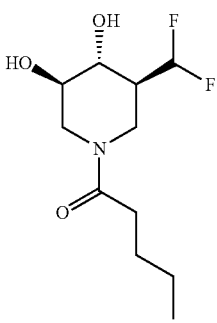 [SMILES: CCCCC(=O)N1C[C@@H](O)[C@H](O)[C@@H](C(F)F)C1] | 1-(3S,4R,5R)-3-(difluoromethyl)-4,5-dihydroxypiperidin-1-yl)pentan-1-one |
| 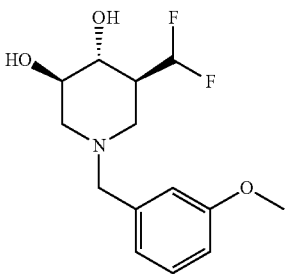 [SMILES: COc1cccc(CN2C[C@@H](O)[C@H](O)[C@@H](C(F)F)C2)c1] | (3R,4R,5S)-5-(difluoromethyl)-1-(3-methoxybenzyl)piperidine-3,4-diol |
| 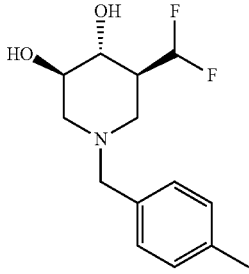 [SMILES: Cc1ccc(CN2C[C@@H](O)[C@H](O)[C@@H](C(F)F)C2)cc1] | (3R,4R,5S)-5-(difluoromethyl)-1-(4-methylbenzyl)piperidine-3,4-diol |
| 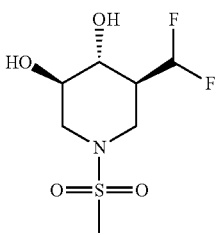 | (3R,4R,5S)-5-(difluoromethyl)-1-(methylsulfonyl)piperidine-3,4-diol |

TABLE 2-continued
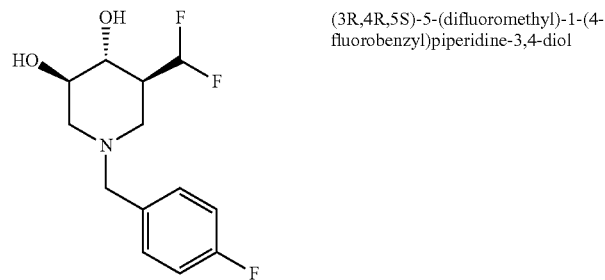
(3R,4R,5S)-5-(difluoromethyl)-1-(4-fluorobenzyl)piperidine-3,4-diol
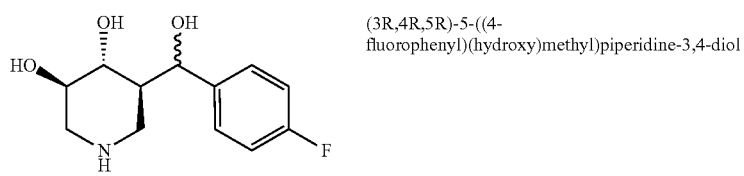
(3R,4R,5R)-5-((4-fluorophenyl)(hydroxy)methyl)piperidine-3,4-diol
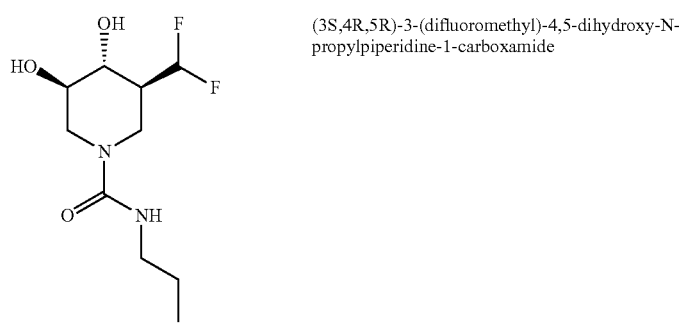
(3S,4R,5R)-3-(difluoromethyl)-4,5-dihydroxy-N-propylpiperidine-1-carboxamide
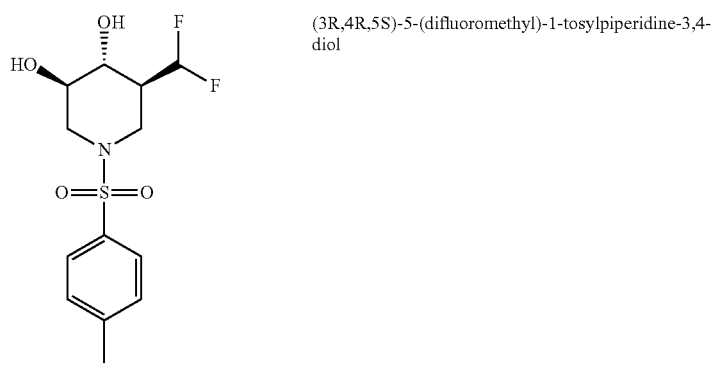
(3R,4R,5S)-5-(difluoromethyl)-1-tosylpiperidine-3,4-diol
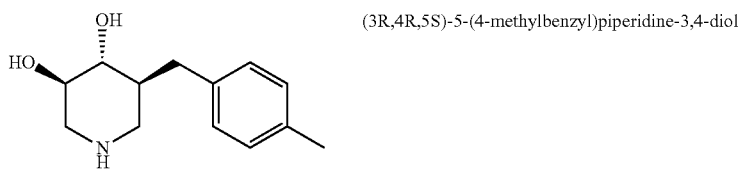
(3R,4R,5S)-5-(4-methylbenzyl)piperidine-3,4-diol

| Structure | Name |
|---|---|
| 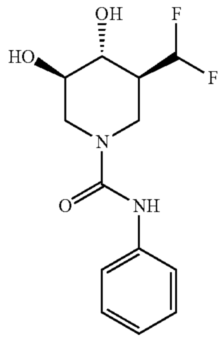 [SMILES: O=C(Nc1ccccc1)N1C[C@@H](O)[C@H](O)[C@@H](C(F)F)C1] | (3S,4R,5R)-3-(difluoromethyl)-4,5-dihydroxy-N-phenylpiperidine-1-carboxamide |
| 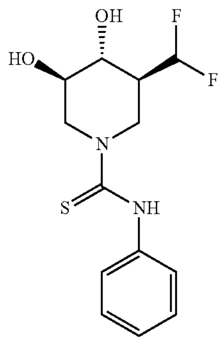 [SMILES: O[C@H]1[C@H](O)CN(C(=S)Nc2ccccc2)C[C@@H]1C(F)F] | (3S,4R,5R)-3-(difluoromethyl)-4,5-dihydroxy-N-phenylpiperidine-1-carbothioamide |
| 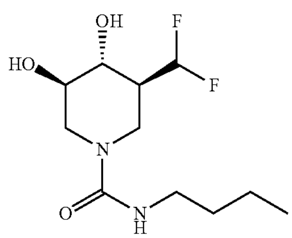 [SMILES: CCCCNC(=O)N1C[C@@H](O)[C@H](O)[C@@H](C(F)F)C1] | (3S,4R,5R)-N-butyl-3-(difluoromethyl)-4,5-dihydroxypiperidine-1-carboxamide |
| 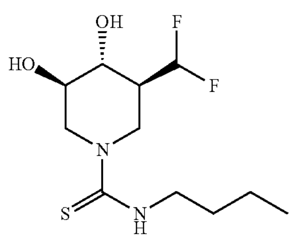 [SMILES: CCCCNC(=S)N1C[C@@H](O)[C@H](O)[C@@H](C(F)F)C1] | (3S,4R,5R)-N-butyl-3-(difluoromethyl)-4,5-dihydroxypiperidine-1-carbothioamide |
| 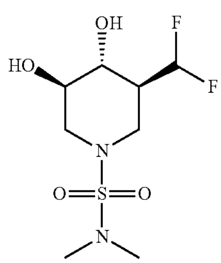 [SMILES: CN(C)S(=O)(=O)N1C[C@@H](O)[C@H](O)[C@@H](C(F)F)C1] | (3S,4R,5R)-3-(difluoromethyl)-4,5-dihydroxy-N,N-dimethylpiperidine-1-sulfonamide |
| 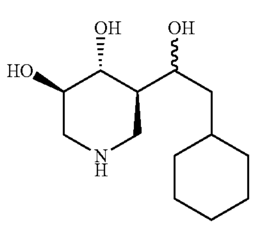 [SMILES: OC(CC1CCCCC1)[C@H]1CNC[C@@H](O)[C@@H]1O] | (3R,4R,5R)-5-(2-cyclohexyl-1-hydroxyethyl)piperidine-3,4-diol |

TABLE 2-continued

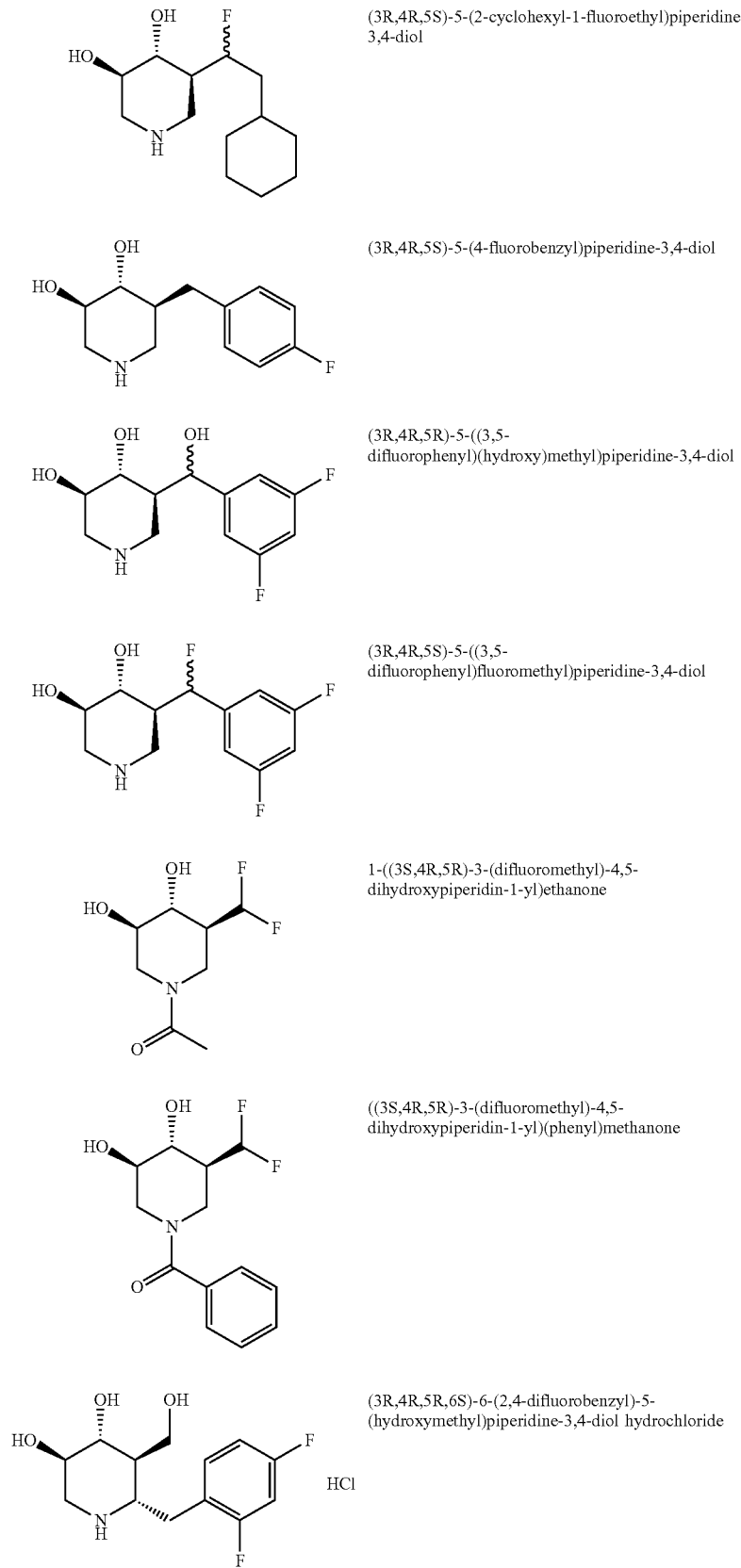

(3R,4R,5S)-5-(2-cyclohexyl-1-fluoroethyl)piperidine-3,4-diol (3R,4R,5S)-5-(4-fluorobenzyl)piperidine-3,4-diol (3R,4R,5R)-5-((3,5-difluorophenyl)(hydroxy)methyl)piperidine-3,4-diol (3R,4R,5S)-5-((3,5-difluorophenyl)fluoromethyl)piperidine-3,4-diol 1-((3S,4R,5R)-3-(difluoromethyl)-4,5-dihydroxypiperidin-1-yl)ethanone ((3S,4R,5R)-3-(difluoromethyl)-4,5-dihydroxypiperidin-1-yl)(phenyl)methanone (3R,4R,5R,6S)-6-(2,4-difluorobenzyl)-5-(hydroxymethyl)piperidine-3,4-diol hydrochloride TABLE 2-continued

| Structure | Name |
|---|---|
| 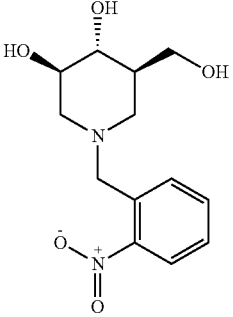 | (3S,4R,5R)-3-fluoro-5-(hydroxymethyl)piperidin-4-ol hydrochloride |
| 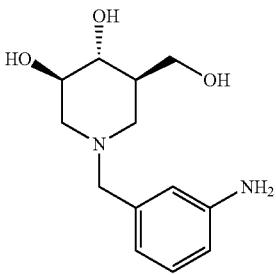 [SMILES: Nc1cccc(CN2C[C@H](CO)[C@@H](O)[C@H](O)C2)c1] | (3R,4R,5R)-5-(hydroxymethyl)-1-(2-nitrobenzyl)piperidine-3,4-diol |
| 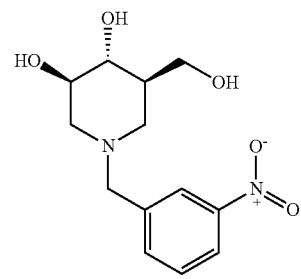 | (3R,4R,5R)-1-(3-aminobenzyl)-5-(hydroxymethyl)piperidine-3,4-diol |
| 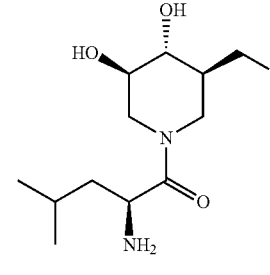 | (3R,4R,5R)-5-(hydroxymethyl)-1-(3-nitrobenzyl)piperidine-3,4-diol |
| 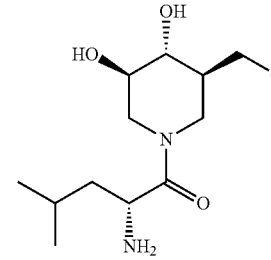 | (S)-2-amino-1-((3R,4R,5R)-3,4-dihydroxy-5-(hydroxymethyl)piperidin-1-yl)-4-methylpentan-1-one |
| 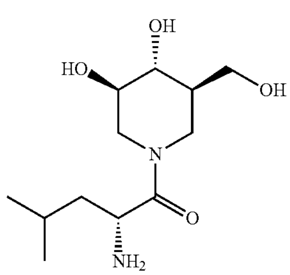 [SMILES: CC(C)C[C@@H](N)C(=O)N1C[C@H](CO)[C@@H](O)[C@H](O)C1] | (R)-2-amino-1-((3R,4R,5R)-3,4-dihydroxy-5-(hydroxymethyl)piperidin-1-yl)-4-methylpentan-1-one |

TABLE 2-continued
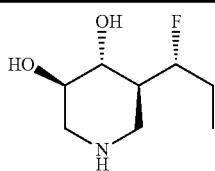
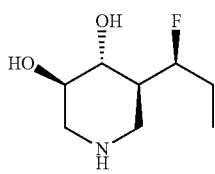
Chemical Process
Compositions of the present invention can be made in accordance of one or more of the following schemes.
Process Scheme 1:
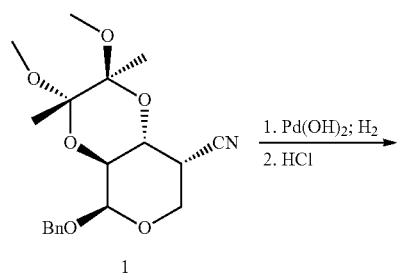
1
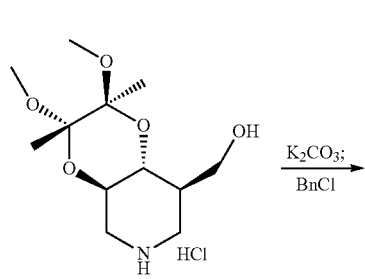
2
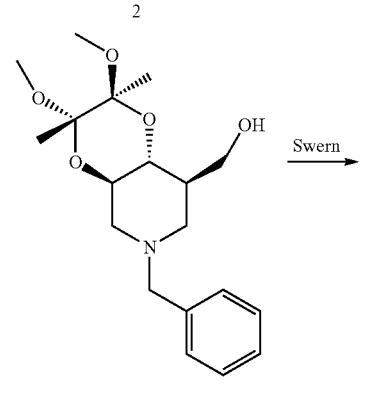
3
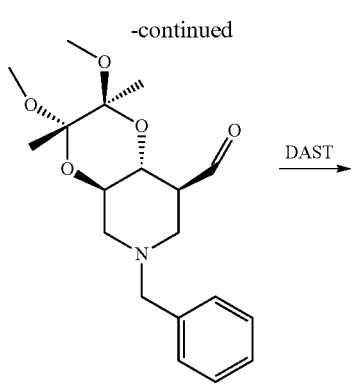
4
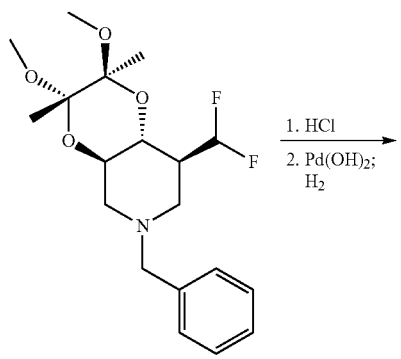
5
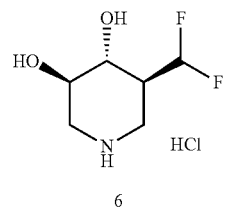 [SMILES: O[C@H]1[C@H](O)CNC[C@@H]1C(F)F ; Cl]
6
((2S,3S,4aR,8R,8aR)-2,3-Dimethoxy-2,3-dimethyl-octahydro-[1,4]dioxino[2,3-c]pyridin-8-yl)methanol Hydrochloride (2)
A solution of 1 (20.0 g, 55.0 mmol) in MeOH (500 mL) was combined with Pd(OH)2 (4-6 g) and ammonium formate (14 g, 220 mmol) and the mixture was heated at 50-55°

C. Additional amounts (3×100.0 mmol) of ammonium formate were added over the next 8 hrs. After the final addition, the reaction mixture was further stirred and heated an additional 16 hrs at 50-55° C. The catalyst was removed by filtration and the filtrate was evaporated in vacuo. The crude product was dissolved in acetone (150 mL), filtered, and HCl in 2-PrOH was added. After seeding and then cooling in an ice bath, the product was collected as a white crystalline solid (11.0 g, 71%). 1H NMR (DMSO-d6) 9.45 (s, 2H), 4.80 (t, 1H, ex), 3.85 (m, 1H), 3.0-3.75 (m, 11H), 2.8 (q, 2H), 1.95 (m, 1H), 1.2 (2, 6H).

((2S,3S,4aR,8R,8aR)-6-Benzyl-2,3-dimethoxy-2,3-dimethyloctahydro-[1,4]dioxino[2,3-c]pyridin-8-yl)methanol (3)

To a solution of 2 (14.85 g, 50.0 mmol) in DMF (200 mL) was added K2CO3 (17.25 g, 125 mmol) and the mixture was stirred at 40° C. for about 4 hrs. At this point, BnCl (5.7 mL, 50.0 mmol) was added in one portion and the reaction was stirred at 40° C. overnight. The solvent was evaporated in vacuo and the residue was suspended in water (600 mL) and HCl was added to dissolve the residue. The solution was washed with Et2O and then basified with Na2CO3. The solution was extracted with EtOAc (2×) and the combined extracts were washed with water and then brine and then dried over MgSO4. The solution was filtered and the filtrate evaporated in vacuo to give the title compound (17.2 g, >95%) as a colorless to very pale yellow viscous oil which was used without further purification. 1H NMR (CDCl3) 7.3 (m, 5H), 3.6-3.8 (m, 2H), 3.5 (s, 3H), 3.4 (t, 1H), 3.26 (s, 3H), 3.268 (s, 3H), 2.9 (m, 2H), 2.2 (br s, 1H), 2.05 (m, 1H), 1.85 (t, 1H), 1.28 (s, 3H), 1.26 (s, 3H).

((2S,3S,4aR,8R,8aR)-6-Benzyl-2,3-dimethoxy-2,3-dimethyloctahydro-[1,4]dioxino[2,3-c]pyridin-8-yl)carboxaldehyde (General Procedure A) (4)

To a solution of DMSO (7.3 g, 96.9 mmol) in CH2Cl2 (150 mL) cooled to −78° C. was added a solution of oxalyl chloride (6.1 mL, 72.8 mmol) in CH2Cl2 dropwise. After the addition was complete the reaction mixture was stirred for an additional 30 min at which point a solution of 3 (17.0 g, 48.4 mmol) in CH2Cl2 was added dropwise. After addition was complete, the reaction was stirred for 1 hr at −78° C. and then diisopropylethylamine (34.4 mL, 193 mmol) was added dropwise. After this addition was complete, the cooling bath was removed and the reaction mixture was allowed to warm to 0° C. when saturated NaHCO3 was added. The mixture was diluted with some additional CH2Cl2 and then the organic layer was separated and dried over MgSO4. After filtering, the solvent was evaporated in vacuo and the crude product was purified by silica gel chromatography (Hex/EtOAc) to give the title compound (12.7 g, 75%) as a viscous oil. 1H NMR (CDCl3) 9.73 (s, 1H), 7.2 (m, 5H), 3.75 (m, 2H), 3.5 (q, 2H), 3.2 (2s, 6H), 2.7-3.0 (m, 3H), 2.05 (m, 2H), 1.25 (2s, 6H).

((2S,3S,4aR,8S,8aR)-6-Benzyl-8,8-difluoromethyl-2,3-dimethoxy-2,3-dimethyloctahydro-[1,4]dioxino[2,3-c]pyridine Hydrochloride (General Procedure B) (5)

To a solution of DAST (1.4 mL, 10.3 mmol) in CH2Cl2 (50 mL) cooled to −15° C. was added a solution of 4 (2.4 g, 6.9 mmol) dropwise. After 10 minutes, the ice bath was removed and the reaction was stirred at room temperature overnight. At this point the reaction mixture was again cooled in an ice bath and the reaction was quenched by addition of saturated NaHCO3 (dropwise at first since this does produce a slight exotherm). The organic layer was separated and dried over Na2SO4, filtered and the solvent was evaporated in vacuo to give a yellow oil. The residue was purified by chromatography on silica gel (Hex/EtOAc) to give the title compound (1.6 g, 62%) as a colorless oil. 1H NMR (CDCl3) 7.2 (m, 5H), 6.0 (dt, 1H), 3.75 (m, 1H), 3.55 (m, 3H), 3.2 (2s, 6H), 2.95 (m, 1H), 2.85 (m, 1H), 2.3 (m, 2H), 1.5 (br s, 1H), 1.2 (2s, 6H).

(3R,4R,5S)-5-(Difluoromethyl)piperdine 3,4-diol Hydrochloride (General Procedure C) (6)

Compound 5 (1.6 g, 4.3 mmol) was heated at reflux in a mixture of EtOH/H2O/HCl (40 mL/40 mL/5 mL) and the reaction monitored by HPLC until the starting material could no longer be detected. The solvent was evaporated in vacuo and then co-evaporated 2× with EtOH. The residue was dissolved in MeOH and hydrogenated over Pd(OH)2. When complete, the catalyst was removed by filtration and the filtrate evaporated in vacuo. The residue was recrystallized from EtOH (50 mL) to the title compound (0.55 g, 66%) as a white solid (mp 168-170° C.). 1H NMR (D2O) 6.15 (dt, 1H), 4.3-4.8 (m, 2H), 3.0 (t, 1H), 2.85 (t, 1H), 2.3 (m, 1H).

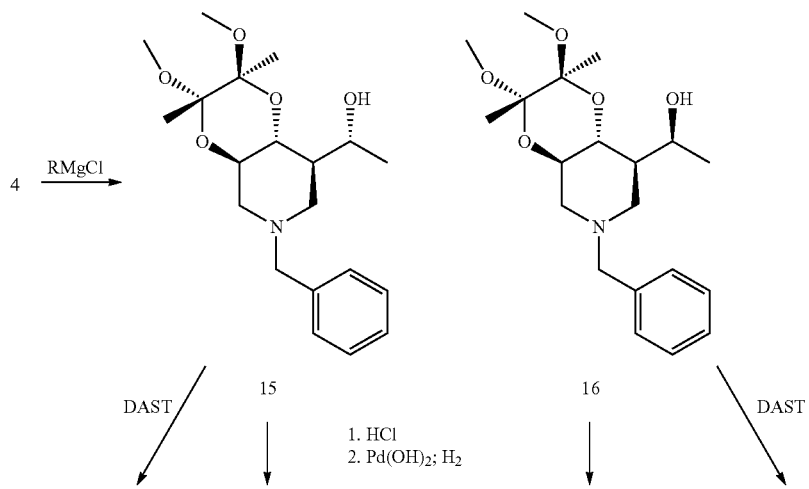

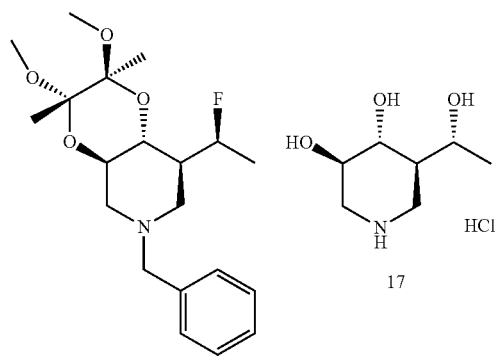

11

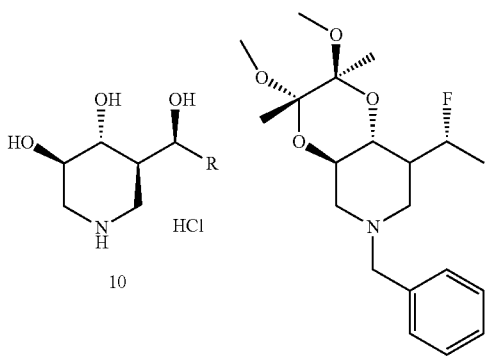

12

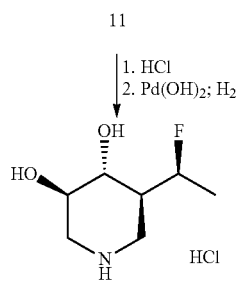

13

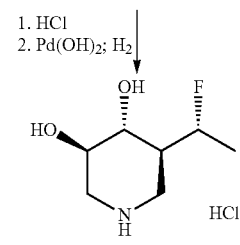

14

(R) and (S)-1-((2S,3S,4aR,8R,8aR)-6-Benzyl-2,3-dimethoxy-2,3-dimethyloctahydro-[1,4]dioxino[2,3-c]pyridin-8-yl)ethanol General Procedure D (15/16)

To a solution of 4 (7.0 g, 20.0 mmol) in dry THF (100 mL) was added MeMgBr (20.0 mL, 1.4M in 3:1 THF/toluene) and the reaction was stirred overnight at room temperature. The reaction was quenched with saturated NH4Cl and the mixture was extracted with EtOAc (2×). The combined extracts were washed with brine, dried over Na2SO4 and the filtrate was evaporated in vacuo. The residue was purified by silica gel chromatography (hexane/2-PrOH) to give the major isomer (15) (1.6 g, 24.6%). 1H NMR (CDCl3). 7.3 (m, 5H), 4.15 (m, 1H), 3.5-3.9 (m, 3H), 3.3 (2s, 6H), 2.85 (m, 2H), 2.0 (2m, 4H), 1.3 (2s, 6H), 1.2 (d, 3H). The minor isomer (16) was also isolated (0.55 g, 7.5%) 7.3 (m, 5H), 3.75 (m, 2H), 3.5 (m, 2H), 3.2 (2s, 6H), 2.8 (m, 2H), 2.0 (t, 1H), 1.75 (m, 2H), 1.2 (2s, 6H), 1.0 (d, 3H).

(3R,4R,5R)-5-((R)-1-Hydroxyethyl)piperdine 3,4-diol (17)

Compound 15 (0.55 g, 1.5 mmol) was stirred in a mixture of 9/1 TFA:H2O (20 mL) until the starting material could no longer be detected by HPLC. The volatiles were removed and the residue was co-evaporated 2-3× with EtOH and then dissolved in EtOH and treated with solid K2CO3. After filtering the solid, the filtrate was evaporated in vacuo, and the residue was converted to an HCl salt and hydrogenated over Pd(OH)2. The catalyst was filtered and the filtrate evaporated in vacuo. The crude product was purified using an ion exchange resin (Dowex 50WX8-200) eluting with 0.1N NH4OH. The appropriate fractions were combined and lyophilized to give the title compound (0.12 g, 50%). 1H NMR (D2O) 4.2 (q, 1H), 3.65 (m, 1H), 3.45 (m, 3H), 2.8 (m, 2H), 1.65 (m, 1H), 1.15 (d, 3H).

(3R,4R,5R)-5-((S)-1-Hydroxyethyl)piperdine 3,4-diol (10)

Compound 16 (0.34 g, 0.93 mmol) was deprotected as described above to give the title compound (0.11 g, 75%).

1H NMR (D20) 4.15 (m, 2H), 3.5 (m, 1H), 3.35 (t, 1H), 3.15 (m, 2H), 1.8 (m, 1H), 1.1 (d, 3H).

((2S,3S,4aR,8R,8aR)-6-Benzyl-8(S)-(1fluoroethyl)-2,3-dimethoxy-2,3-dimethyloctahydro-[1,4]dioxino[2,3-c]pyridine (11)

Compound 15 (1.8 g, 5.0 mmol) was fluorinated using General Procedure B. Silica gel chromatography (Hex/EtOAc) gave the title compound (0.42 g, 23%). 1H NMR (CDCl3) 7.25 (m, 5H), 4.7-4.9 (dq, 1H), 3.75 (m, 2H), 3.4 (m, 2H), 3.2 (2s, 6H), 2.8 (m, 2H), 2.0 (m, 3H), 1.35 (dd, 3H), 1.2 (2s, 6H).

(3R,4R,5R)-5((S)-1-Fluoroethyl)piperidine 3,4-diol Hydrochloride (13)

Compound 11 (0.42 g, 1.14 mmol) was deprotected as described in General Procedure C. After catalyst was removed, the filtrate was evaporated in vacuo and then co-evaporated with EtOH (2×). The resulting residue was triturated with acetone to give the title compound (0.20 g, 88%) as a white solid. 1H NMR (DMSO-d6) 9.0 (br s, 2H), 5.6 (d, 1H, ex), 5.4 (d, 1H, ex), 5.0-5.2 (dq, 1H), 3.55 (m, 1H), 3.2 (m, 2H), 2.9 (t, 1H), 2.7 (t, 1H), 2.2 (m, 1H), 1.3 (dd, 3H).

((2S,3S,4aR,8R,8aR)-6-Benzyl-8(R)-(1fluoroethyl)-2,3-dimethoxy-2,3-dimethyloctahydro-[1,4]dioxino[2,3-c]pyridine (12)

Compound 16 (0.55 g, 1.5 mmol) was fluorinated using General Procedure B to give the title compound (0.22 g, 40%). 1H NMR (CDCl3) 7.3 (m, 5H), 5.0 (dq, 1H), 3.8 (m, 1H), 3.5-3.75 (m, 3H), 3.3 (2s, 6H), 3.0 (d, 1H), 2.9 (m, 1H), 2.1 (m, 2H), 1.85 (m, 1H), 1.3 (2s, 6H).

(3R,4R,5R)-5((R)-(1-Fluoroethyl)piperdine 3,4-diol Hydrochloride (14)

Compound 12 (0.22 g, 0.6 mmol) was deprotected as described in General Procedure C. After catalyst was removed, the filtrate was evaporated in vacuo and then co-evaporated with EtOH (2×). The resulting residue was triturated with acetone to give the title compound (0.08 g, 67%) as a white solid. 1H NMR (D20) 5.1 (dq, 1H), 3.5 (m, 4H), 2.8 (m, 2H), 1.8 (m, 1H), 1.3 (dd, 3H).

Process Scheme 2:

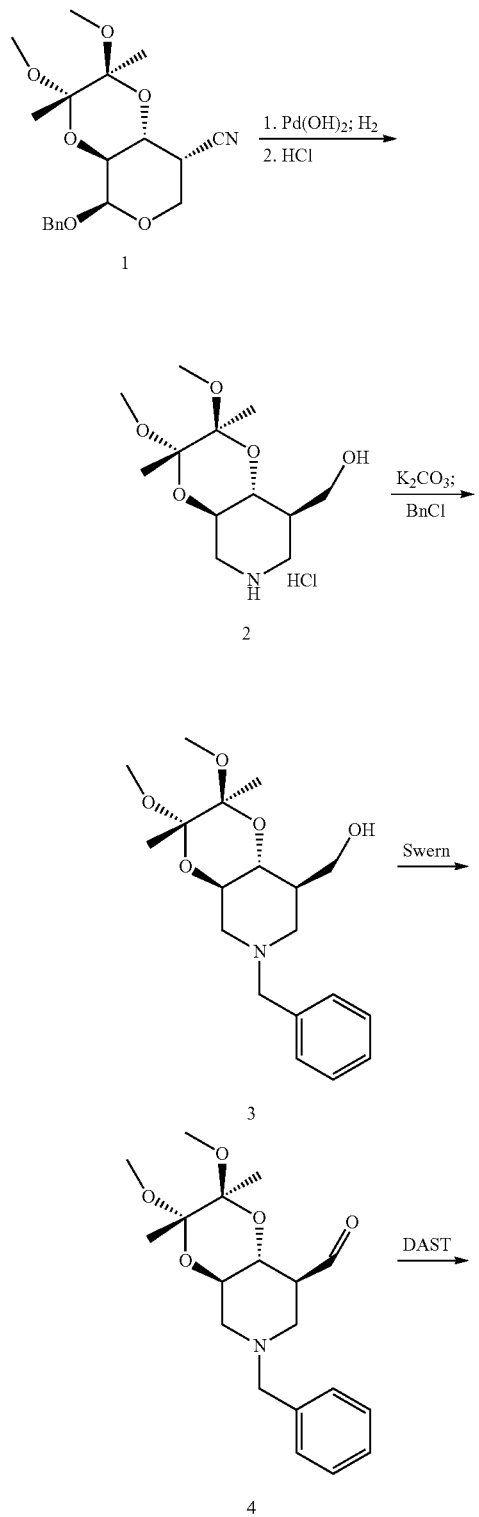

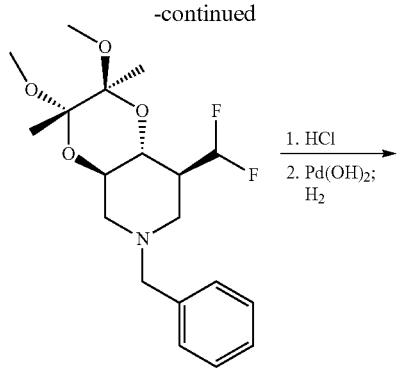

((2S,3S,4aR,8R,8aR)-2,3-Dimethoxy-2,3-dimethyl-octahydro-[1,4]dioxino[2,3-c]pyridin-8-yl)methanol Hydrochloride (2)

A solution of 1 (20.0 g, 55.0 mmol) in MeOH (500 mL) was combined with Pd(OH)$_2$ (4-6 g) and ammonium formate (14 g, 220 mmol) and the mixture was heated at 50-55° C. Additional amounts (3×100.0 mmol) of ammonium formate were added over the next 8 hrs. After the final addition, the reaction mixture was further stirred and heated an additional 16 hrs at 50-55° C. The catalyst was removed by filtration and the filtrate was evaporated in vacuo. The crude product was dissolved in acetone (150 mL), filtered, and HCl in 2-PrOH was added. After seeding and then cooling in an ice bath, the product was collected as a white crystalline solid (11.0 g, 71%). $^1$H NMR (DMSO-d$_6$) 9.45 (s, 2H), 4.80 (t, 1H, ex), 3.85 (m, 1H), 3.0-3.75 (m, 11H), 2.8 (q, 2H), 1.95 (m, 1H), 1.2 (2, 6H).

((2S,3S,4aR,8R,8aR)-6-Benzyl-2,3-dimethoxy-2,3-dimethyloctahydro-[1,4]dioxino[2,3-c]pyridin-8-yl)methanol (3)

To a solution of 2 (14.85 g, 50.0 mmol) in DMF (200 mL) was added K$_2$CO$_3$ (17.25 g, 125 mmol) and the mixture was stirred at 40° C. for about 4 hrs. At this point, BnCl (5.7 mL, 50.0 mmol) was added in one portion and the reaction was stirred at 40° C. overnight. The solvent was evaporated in vacuo and the residue was suspended in water (600 mL) and HCl was added to dissolve the residue. The solution was washed with Et$_2$O and then basified with Na$_2$CO$_3$. The solution was extracted with EtOAc (2×) and the combined extracts were washed with water and then brine and then dried over MgSO$_4$. The solution was filtered and the filtrate evaporated in vacuo to give the title compound (17.2 g, >95%) as a colorless to very pale yellow viscous oil which was used without further purification. $^1$H NMR (CDCl$_3$) 7.3 (m, 5H), 3.6-3.8 (m, 2H), 3.5 (s, 3H), 3.4 (t, 1H), 3.26 (s, 3H), 3.268 (s, 3H), 2.9 (m, 2H), 2.2 (br s, 1H), 2.05 (m, 1H), 1.85 (t, 1H), 1.28 (s, 3H), 1.26 (s, 3H).

((2S,3S,4aR,8R,8aR)-6-Benzyl-2,3-dimethoxy-2,3-dimethyloctahydro-[1,4]dioxino[2,3-c]pyridin-8-yl)carboxaldehyde (General Procedure A) (4)

To a solution of DMSO (7.3 g, 96.9 mmol) in CH$_2$Cl$_2$ (150 mL) cooled to −78° C. was added a solution of oxalyl chloride (6.1 mL, 72.8 mmol) in CH$_2$Cl$_2$ dropwise. After the addition was complete the reaction mixture was stirred for an additional 30 min at which point a solution of 3 (17.0 g, 48.4 mmol) in CH$_2$Cl$_2$ was added dropwise. After addition was complete, the reaction was stirred for 1 hr at −78° C. and then diisopropylethylamine (34.4 mL, 193 mmol) was added dropwise. After this addition was complete, the cooling bath was removed and the reaction mixture was allowed to warm to 0° C. when saturated NaHCO$_3$ was added. The mixture was diluted with some additional CH$_2$Cl$_2$ and then the organic layer was separated and dried over MgSO$_4$. After filtering, the solvent was evaporated in vacuo and the crude product was purified by silica gel chromatography (Hex/EtOAc) to give the title compound (12.7 g, 75%) as a viscous oil. $^1$H NMR (CDCl$_3$) 9.73 (s, 1H), 7.2 (m, 5H), 3.75 (m, 2H), 3.5 (q, 2H), 3.2 (2s, 6H), 2.7-3.0 (m, 3H), 2.05 (m, 2H), 1.25 (2s, 6H).

((2S,3S,4aR,8S,8aR)-6-Benzyl-8,8-difluoromethyl-2,3-dimethoxy-2,3-dimethyloctahydro-[1,4]dioxino[2,3-c]pyridine Hydrochloride (General Procedure B) (5)

To a solution of DAST (1.4 mL, 10.3 mmol) in CH$_2$Cl$_2$ (50 mL) cooled to −15° C. was added a solution of 4 (2.4 g, 6.9 mmol) dropwise. After 10 minutes, the ice bath was removed and the reaction was stirred at room temperature overnight. At this point the reaction mixture was again cooled in an ice bath and the reaction was quenched by addition of saturated NaHCO$_3$ (dropwise at first since this does produce a slight exotherm). The organic layer was separated and dried over Na$_2$SO$_4$, filtered and the solvent was evaporated in vacuo to give a yellow oil. The residue was purified by chromatography on silica gel (Hex/EtOAc) to give the title compound (1.6 g, 62%) as a colorless oil. $^1$H NMR (CDCl$_3$) 7.2 (m, 5H), 6.0 (dt, 1H), 3.75 (m, 1H), 3.55 (m, 3H), 3.2 (2s, 6H), 2.95 (m, 1H), 2.85 (m, 1H), 2.3 (m, 2H), 1.5 (br s, 1H), 1.2 (2s, 6H).

(3R,4R,5S)-5-(Difluoromethyl)piperdine 3,4-diol Hydrochloride (General Procedure C) (6)

Compound 5 (1.6 g, 4.3 mmol) was heated at reflux in a mixture of EtOH/H$_2$O/HCl (40 mL/40 mL/5 mL) and the reaction monitored by HPLC until the starting material could no longer be detected. The solvent was evaporated in vacuo and then co-evaporated 2× with EtOH. The residue was dissolved in MeOH and hydrogenated over Pd(OH)$_2$. When complete, the catalyst was removed by filtration and the filtrate evaporated in vacuo. The residue was recrystallized from EtOH (50 mL) to the title compound (0.55 g, 66%) as a white solid (mp 168-170° C.). $^1$H NMR (D$_2$O) 6.15 (dt, 1H), 4.3-4.8 (m, 2H), 3.0 (t, 1H), 2.85 (t, 1H), 2.3 (m, 1H).

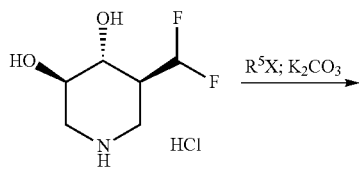

6

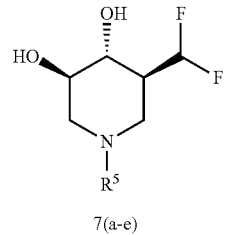

7(a-e)

(3R,4R,5S)-1.Butyl-5-(difluoromethyl)piperdine 3,4-diol (General Procedure D) (7a; R$^5$=Bu)

A mixture of 6 (0.30 g, 1.4 mmol), K$_2$CO$_3$ (0.48 g, 3.5 mmol) and BuBr (0.20 g, 1.4 mmol) was combined in DMF (10 mL) and heated overnight at 60° C. The solvent was evaporated in vacuo and the residue was dissolved in EtOAc, washed with water and then brine and dried over Na$_2$SO$_4$. After filtration, the filtrate was evaporated in vacuo to give the crude product which was purified by chromatography (CH$_2$Cl$_2$/(9:1) MeOH/NH$_4$OH) to give the title compound (0.25 g, 80%) as a colorless sirup. MH$^+$=224. $^1$H NMR (DMSO-d$_6$) 6.2 (t, 1H, J=57 Hz), 5.13 (d, 1H, ex), 4.91 (d, 1H, ex), 3.3 (m, 1H), 3.1 (m, 1H), 2.9 (m, 2H), 2.3 (m, 2H), 1.95 (m, 2H), 1.75 (t, 1H), 1.2-1.5 (2m, 4H), 0.9 (t, 3H).

(3R,4R,5S)-1.Allyl-5-(difluoromethyl)piperdine 3,4-diol (7b; R$^5$=allyl)

Following General Procedure D using allyl bromide (0.17 g, 1.4 mmol) the tile compound was obtained as a white solid (0.22 g, 76%). MH$^+$=208. $^1$H NMR (DMSO-d$_6$) 6.2 (t, 1H, J=57 Hz), 5.8 (m, 1H), 5.2 (m, 3H), 4.92 (d, 1H), 3.3 (m, 1H), 3.1 (1H), 2.95 (d, 2H), 2.85 (d, 2H), 1.9 (br m, 2H), 1.75 (t, 1H).

(3R,4R,5S)-5-(Difluoromethyl)-1-(4-fluorobenzyl)piperdine 3,4-diol (7c; R$^5$=4-fluorobenzyl)

Following General Procedure D except that reaction was run at room temperature and using 4-fluorobenzyl bromide (0.26 g, 1.4 mmol) the tile compound was obtained as a white solid (0.22 g, 56%). MH$^+$=276. $^1$H NMR (DMSO-d$_6$) 7.4 (m, 2H), 7.15 (m, 2H), 6.2 (t, 1H, J=57 Hz), 5.2 (d, 1H, ex), 4.9 (d, 1H, ex), 3.5 (q, 2H), 3.3 (m, 1H), 3.1 (m, 1H), 2.8 (m, 2H), 2.0 (m, 2H), 1.8 (t, 1H).

(3R,4R,5S)-5-(Difluoromethyl)-1-(4-methylbenzyl)piperdine 3,4-diol (7d; R$^5$=4-methylbenzyl)

Following General Procedure D except that reaction was run at room temperature and using 4-methylbenzyl bromide (0.26 g, 1.4 mmol) the tile compound was obtained as a white solid (0.30, 81%). MH$^+$=272. $^1$H NMR (DMSO-d$_6$) 7.2 (m, 4H), 6.2 (t, 1H, J=57 Hz), 5.2 (d, 1H, ex), 4.9 (d, 1H, ex), 3.5 (q, 2H), 3.3 (1H), 3.05 (m, 1H), 2.8 (m, 2H), 2.5 (s, 3H), 1.95 (m, 2H), 1.8 (t, 1H).

(3R,4R,5S)-5-(Difluoromethyl)-1-(4-methoxylbenzyl)piperdine 3,4-diol (7e; R$^5$=4-methoxylbenzyl)

Following General Procedure D except that reaction was run at room temperature and using 4-methoxylbenzyl chloride (0.26 g, 1.4 mmol) the tile compound was obtained as a colorless sirup (0.19 g, 49%). MH⁺=288. ¹H NMR (DMSO-d₆) 7.3 (m, 1H), 6.85 (m, 3H) 6.2 (t, 1H, J=57 Hz), 5.2 (d, 1H, ex), 4.9 (d, 1H, ex), 3.75 (s, 3H), 3.5 (q, 2H), 3.4 (m, 1H), 3.1 (m, 1H), 2.85 (m, 2H), 1.95 (m, 2H), 1.8 (t, 1H).

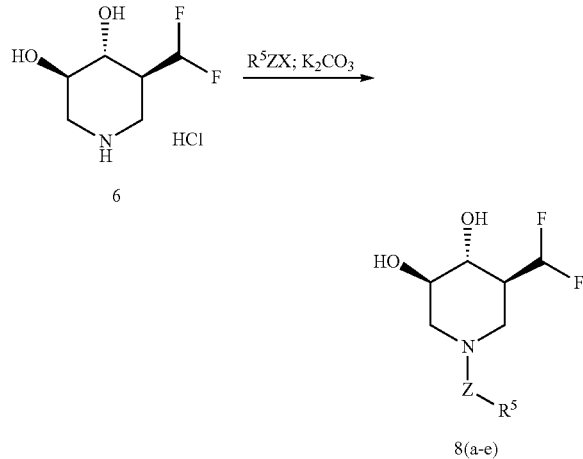

1-((3S,4R,5R)-3-(Difluoromethyl)-4,5-dihydroxypiperdine-1-yl)pentane-1-one (8a; Z=CO; R⁵=butyl)

Following General Procedure D, except that the reaction was run at room temperature and using pentanoyl chloride (0.17 g, 1.4 mmol), the title compound was obtained as a white solid (0.26 g, 71%). MH⁺=252. ¹H NMR (DMSO-d₆) 5.9-6.5 (dt, 1H), 5.35 (m, 1H, ex), 5.25 (m, 1H), ex), 4.2 (dd, 1H), 3.75 (dd, 1H), 3.35 (m, 2H), 3.1 (m, 1H), 2.85 (m, 1H), 2.3 (t, 2H), 1.9 br m, 1H), 1.4 (m, 2H), 1.25 (m, 2H), 0.85 (t, 3H).

(3R,4R,5S)-5-(Difluoromethyl)-1-(methanesulfonyl) piperidine 3,4-diol (8b; Z=SO₂; R⁵=Me)

Following General Procedure D except that the reaction was run at room temperature and using methanesulfonyl chloride (0.16 g, 1.4 mmol), the title compound was obtained as a white solid (0.17 g, 51%). ¹H NMR (DMSO-d₆) 6.2 (t, 1H, J=53 Hz), 5.43 (d, 1H, ex), 5.38 (d, 1H, ex), 3.2-3.7 (m, 4H), 2.95 (s, 3H), 2.85 (m, 1H), 2.7 (t, 1H), 2.1 (br s, 1H). (3R,4R,5S)-5-(Difluoromethyl)-1-tosylpiperdine 3,4-diol (8b; Z=SO₂; R⁵=Ph) Following General Procedure D except that the reaction was run at room temperature and using toluenesulfonyl chloride (0.26, 1.4 mmol), the title compound was obtained as a white solid (0.35 g, 67%). ¹H NMR (DMSO-d₆) 7.6 (d, 2H), 7.45 (d, 2H), 6.25 (t, 1H, J=53 Hz), 5.4 (2d, 2H, ex), 3.3-3.55 (m, 4H), 3.2 (m, 1H), 2.5 (m, 3H), 2.4 (t, 1H), 2.1 (m, 1H).

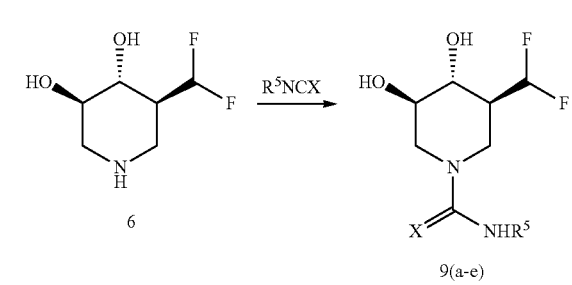

(3S,4R,5R)-3-(Difluoromethyl)-4,5-dihydroxy-N-propylpiperdine-1-carboxamide (General Procedure E) (9a; X=O; R⁵=propyl)

To a solution of 6 (free base) (0.29 g, 1.2 mmol) in dry DMF (5 mL), was added propyl isocyanate (0.10 g, 1.2 mmol) and the reaction was stirred at room temperature overnight. The solvent was evaporated in vacuo and the residue was purified by chromatography (CH₂Cl₂/MeOH) to give the title compound as a white solid (0.14 g, 48%). MH⁺=253. ¹H NMR (DMSO-d₆) 6.7 (t, 1H), 6.22 (t, 1H, J=53 Hz), 5.25 (d, 1H, ex), 5.15 (d, 1H, ex), 4.05 (d, 1H), 3.9 (d, 1H), 3.3 (m, 2H), 3.0 (q, 2H), 2.5 (m, 1H), 1.8 (br d, 1H), 1.4 (m, 2H), 0.85 (t, 3H).

(3S,4R,5R)-3-(Difluoromethyl)-4,5-dihydroxy-N-phenylpiperdine-1-carboxamide (9b; X=O; R⁵=phenyl)

Following General Procedure E and using phenyl isocyanate (0.14 g, 1.2 mmol) the title compound was obtained as a white solid (0.21 g, 62%). MH⁺=287. ¹H NMR (DMSO-d₆) 8.7 (s, 1H), 7.45 (d, 2H), 7.3 (t, 2H), 6.95 (t, 1H), 6.3 (t, 1H, J=53 Hz), 5.35 (d, 1H), 5.25 (d, 1H), 4.1 (t, 2H), 3.3 (m, 2H), 2.85 (t, 1H), 2.75 (t, 1H), 1.95 (br 1H).

(3S,4R,5R)-3-(Difluoromethyl)-4,5-dihydroxy-N-butylpiperdine-1-carboxamide (9c; X=O; R⁵=butyl)

Following General Procedure E and using butyl isocyanate (0.12 g, 1.2 mmol) the title compound was obtained as a white solid (0.24 g, 76%). MH⁺=267. ¹H NMR (DMSO-d₆) 6.6 (t, 1H), 6.2 (t, 1H, J=53 Hz), 5.25 (d, 1H), 5.1 (d, 1H), 4.05 (d, 1H), 3.9 (d, 1H), 3.35 (m, 2H), 3.05 (q, 2H), 2.65 (t, 1H), 2.45 (m, 1H), 1.8 (br d, 1H), 1.2-1.4 (2m, 4H), 0.85 (t, 3H).

(3S,4R,5R)-3-(Difluoromethyl)-4,5-dihydroxy-N-butylpiperdine-1-carbthioamide (9d; X=S; R⁵=butyl)

Following General Procedure E and using butyl isothiocyanate (0.14 g, 1.2 mmol) the title compound was obtained as a colorless sirup (0.21 g, 63%). MH⁺=283. ¹H NMR (DMSO-d₆) 7.85 (t, 1H), 6.25 (t, 1H), 5.35 (2d, 2H), 4.8 (d, 1H), 4.45 (d, 1H), 3.45 (m, 2H), 3.25 (m, 1H), 3.05 (t, 1H), 2.8 (t, 1H), 1.85 (br d, 1H), 1.4 (m, 2H), 1.35 (m, 2H), 1.1 (m, 1H), 0.95 (t, 3H).

(3S,4R,5R)-3-(Difluoromethyl)-4,5-dihydroxy-N-phenylpiperdine-1-carbthioamide (9e; X=S; R⁵=phenyl)

Following General Procedure E and using phenyl isothiocyanate (0.16 g, 1.2 mmol) the title compound was obtained as a white solid (0.31 g, 86%). MH⁺=303. ¹H NMR (DMSO-d₆) 9.5 (s, 1H), 7.3 (m, 4H), 7.1 (t, 1H), 6.35 (t, 1H), 5.35 (2d, 2H), 4.85 (d, 1H), 4.55 (d, 1H), 3.45 (m, 2H), 3.2 (t, 1H), 3.0 (t, 1H), 2.05 (br d, 1H).

Compounds of the present invention can also be made by one skilled in the art using the following general schemes:

Scheme 3
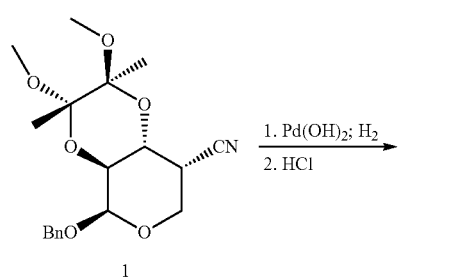
1
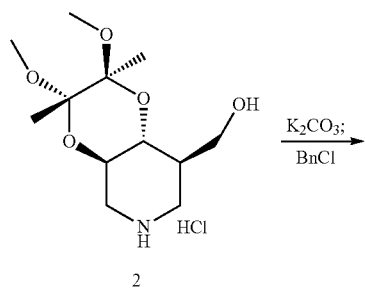
2
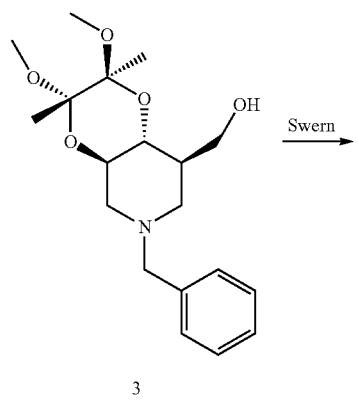
3
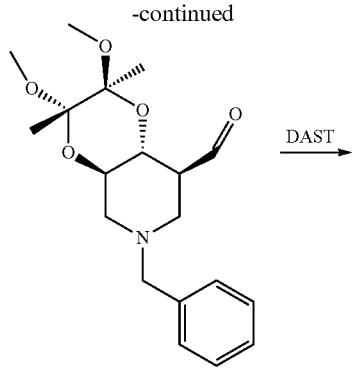
4
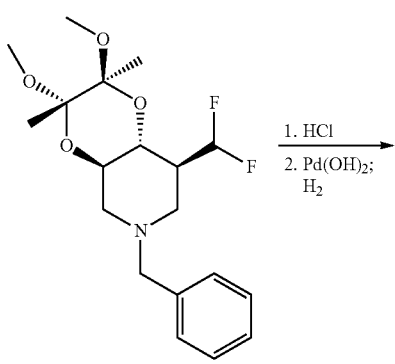
5
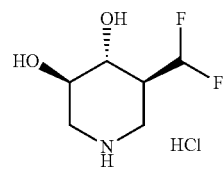
6
Scheme 4
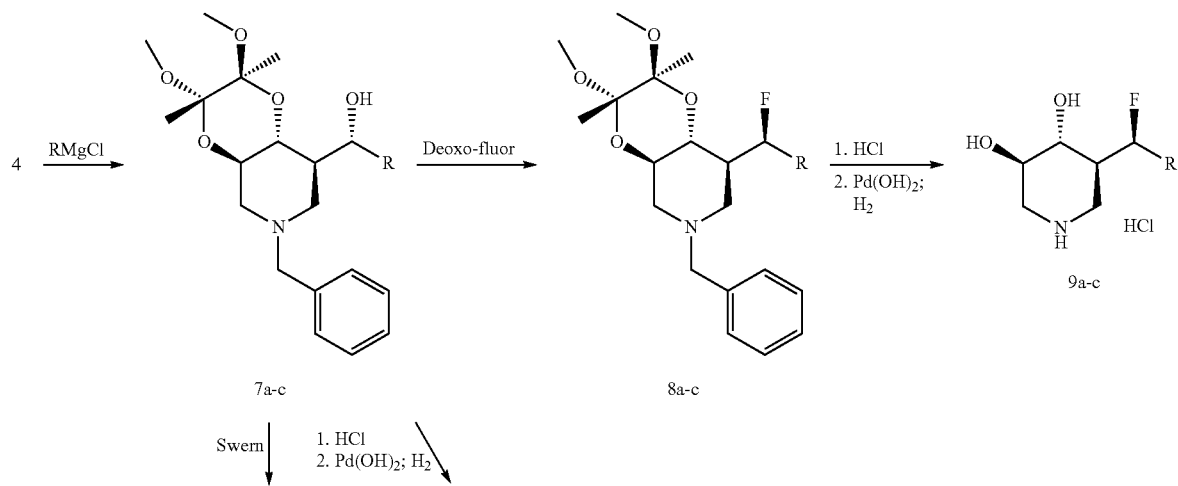

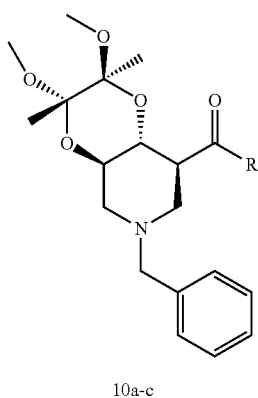
10a-c
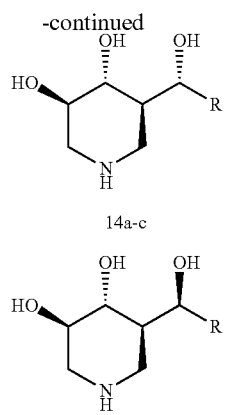
14a-c
15a-c
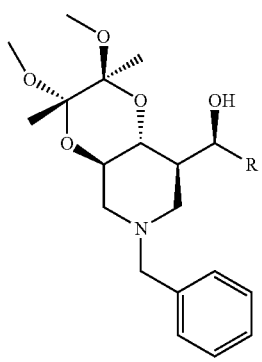
11a-c
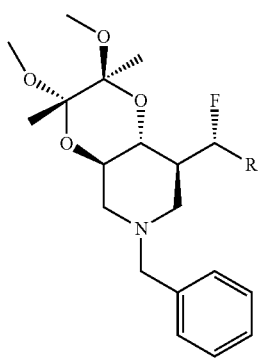
12a-c
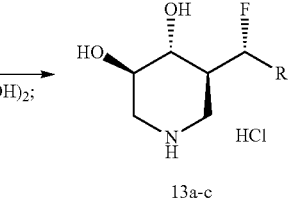
13a-c
Scheme 5
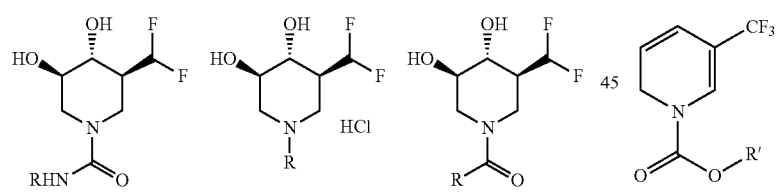
Scheme 6
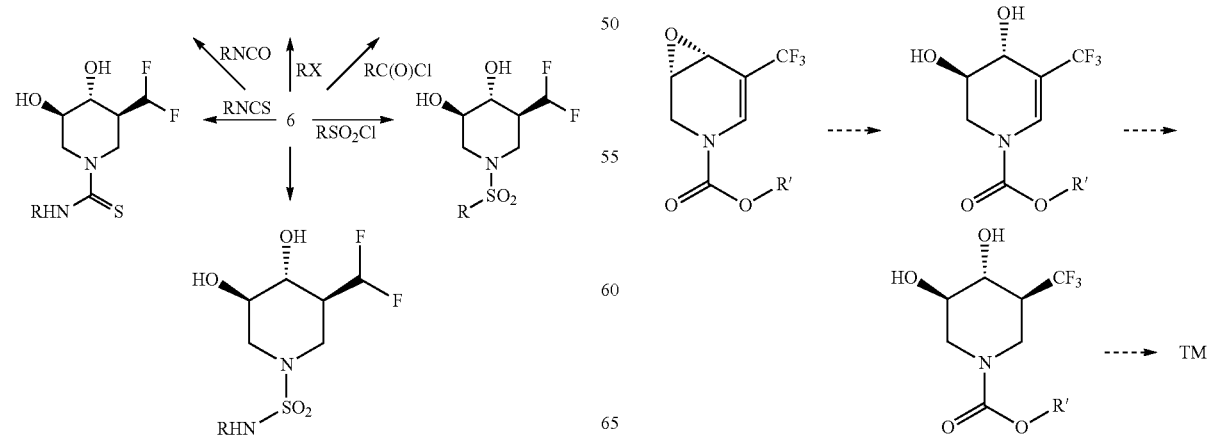

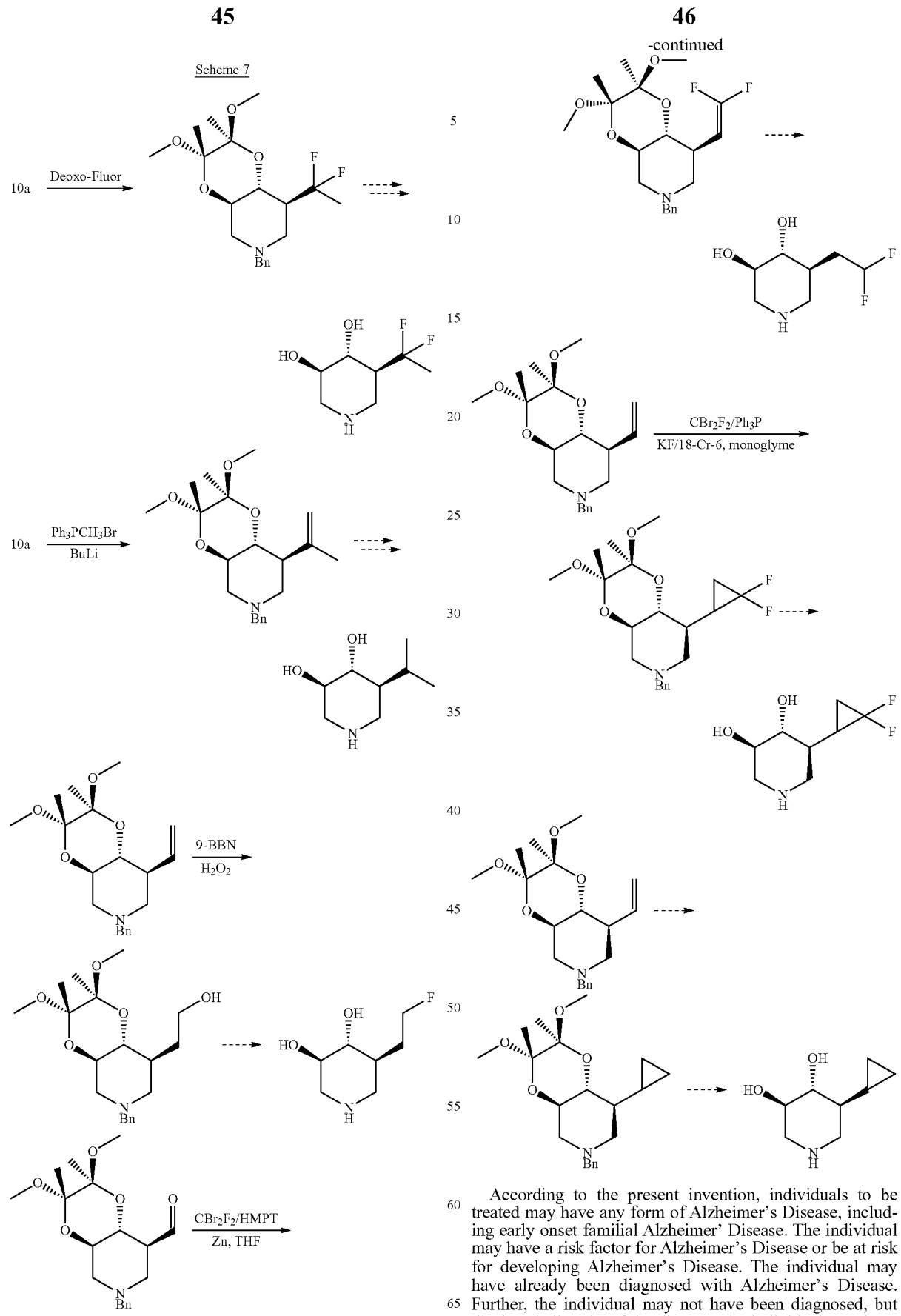

According to the present invention, individuals to be treated may have any form of Alzheimer's Disease, including early onset familial Alzheimer' Disease. The individual may have a risk factor for Alzheimer's Disease or be at risk for developing Alzheimer's Disease. The individual may have already been diagnosed with Alzheimer's Disease. Further, the individual may not have been diagnosed, but displays hallmarks of the disease. The individual may have or may be at risk for developing Progressive supranuclear palsy, Corticobasal degenerations and/or Frontotemporal lobar degeneration (Pick's disease). In a further embodiment, Alzheimer's Disease is caused by or linked to Down syndrome.

Further, the claimed treatment may include combinations of one or more pharmacological chaperones and may also be combined with other known Alzheimer treatments or any condition related to or resulting from the pathological aggregation of tau protein. Treatment may also include combinations of one, two, three or more pharmacological chaperones or a combination of one, two, three or more chaperones with one or more inhibitors of glucosylceramide synthase. Combination therapies including one or more chaperones with one or more inhibitors of glucosylceramide synthase and may increase ganglioside activity and decrease glucosylceramide synthase activity. Treatment may also include combinations of one, two, three or more pharmacological chaperones with one or more inhibitors of O-GlcNAcase (OGA). Examples of pharmacological chaperone combinations may include, for example:

NGT, zanamivir
AdDNJ, zanamivir

Examples of pharmacological chaperone and substrate replacement therapy (SRT) combinations may include, for example:

NGT, NB-DNJ
NGT, NB-DGJ
NGT, zanamivir, NB-DGJ
NGT, zanamivir, NB-DNJ
NB-DNJ, zamamivir
NB-DGJ, zanamivir
AdDNJ, NB-DNJ
AdDNJ, NB-DGJ
AdDNJ, zanamivir, NB-DNJ
AdDNJ, zanamivir, NB-DGJ The present invention is also directed to a method for the treatment of a condition resulting from the pathological aggregation of Tau protein, such as Frontotemporal demential, Progressive supranuclear palsy, Corticobasal degenerations and Frontotemporal lobar degeneration.

Figure 5:
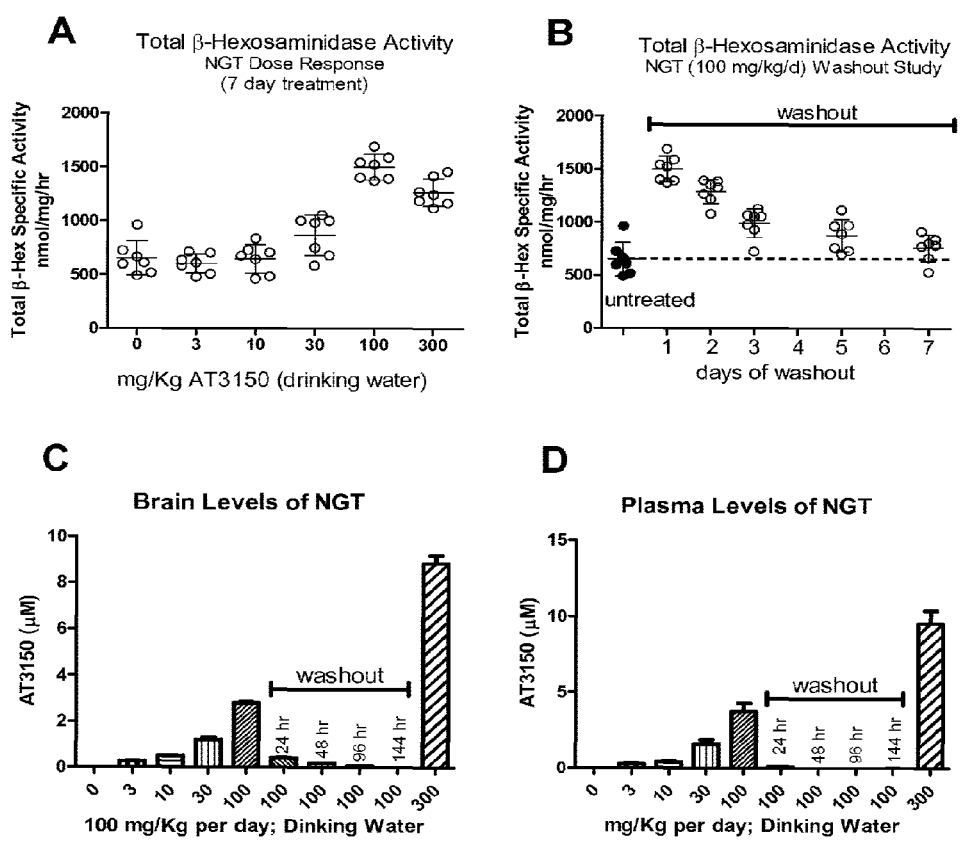
FIG. 5 shows the effects of dose and washout on endogenous wild-type β-hexosaminidase activity in brains of C57BL6 mice treated with the pharmacological chaperone NGT and corresponding drug levels in brain and plasma.
Figure 6:
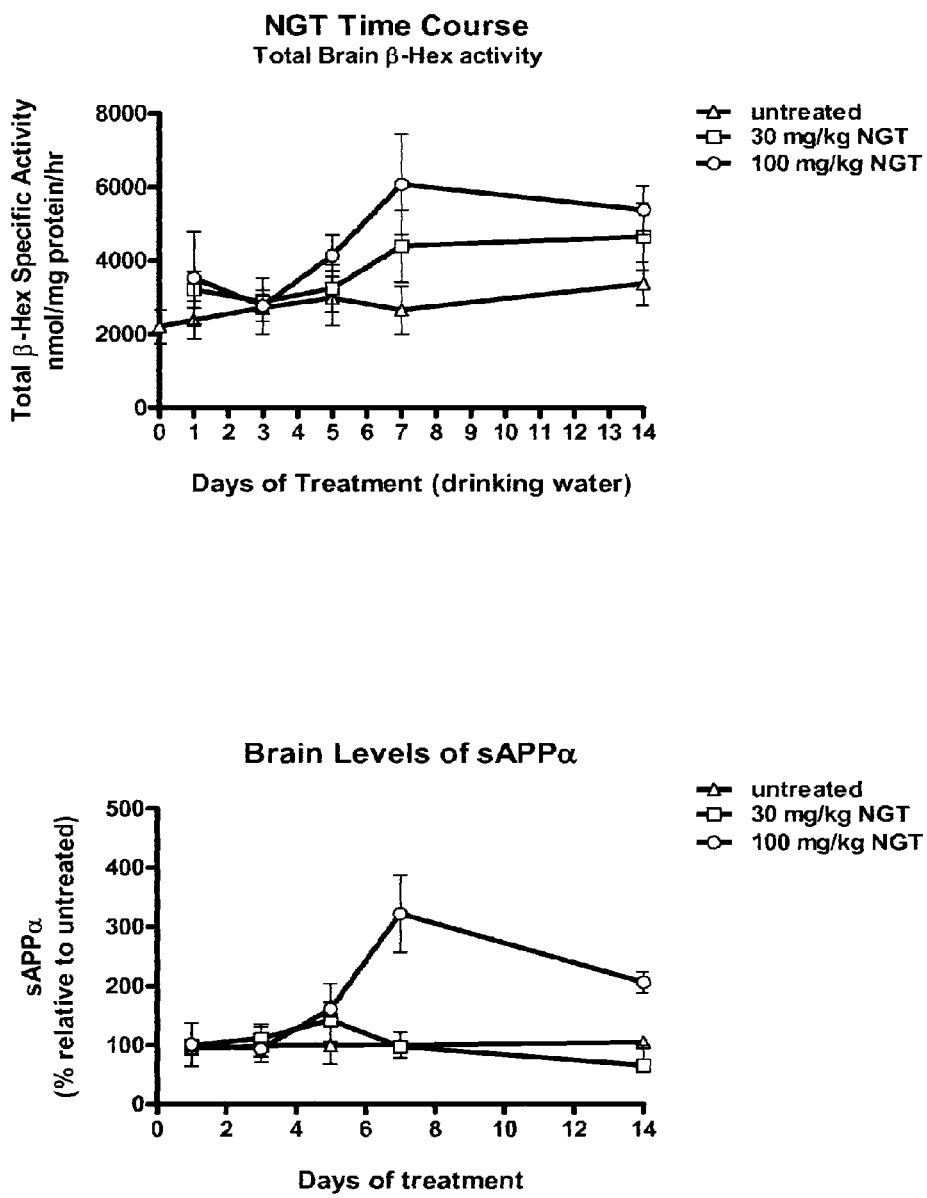
FIG. 6 shows a time course for the effects of the pharmacological chaperone NGT on endogenouse wild-type levels of β-hexosaminidase activity and sAPPα levels in the brains of C57BL6 mice.
Figure 7:
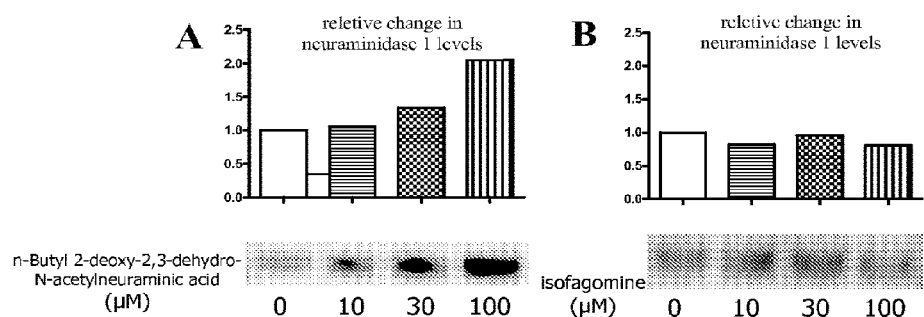
FIG. 7 shows the enhancement of neuraminidase 1 levels in fibroblasts due to the pharmacological chaperone NB-DANA.

NGT is one of the pharmacological chaperones listed in Table 1. NGT increases mutant β-hexosaminidase activity in patient-derived cells and endogenous wild-type β-hexosaminidase activity in C57BL6 mice. NGT has good in vivo PK properties, including blood brain barrier penetration, is selective for β-hexosaminidase and is well-tolerated. NGT is stable, water soluble, and has good oral bioavailability. It selectively increases the levels of wild-type β-hexosaminidase activity in the brains of C57BL6 mice and increase levels of neurotrophic sAPPα (FIGS. 5 and 6).

n-butyl-2-deoxy-2,3-dehydro-N-acetylneuraminic acid is also a pharmacological chaperone listed in Table 1. n-butyl-2-deoxy-2,3-dehydro-N-acetylneuraminic acid selectively increases wild type neuraminidase 1 activity in fibroblasts derived from healthy controls (FIG. 7).

Studies have shown that β-Hexosaminidase deficient mice have amyloid-like deposits and pThr231-Tau immunoreactivity. In vitro studies have shown that purified gangliosides can induce Aβ oligomerization and fibril formation. GLB1 KO mice accumulate GM1 and GA1 gangliosides throughout the brain. Sango, et al., Nat. Genet. 11(2): 170-176 (1995). While the HEXB KO mice accumulate GM2 and GA2 gangliosides in neurons throughout the brain and spinal cord. Hahn, et al., Hum. Mol. Genet. 6(2): 205-211 (1997). Preliminary IHC analyses of the brain and spinal cord of 4 month old HEXB KO mice revealed the presence of deposits that immunoreacted with anti-rodent-Aft No such Aβ-immunoreactive deposits were seen in the brains and spinal cords of age-matched wild-type control mice.

NGT can increase endogenous wild-type β-hexosaminidase activity in cell culture and in the brains of C57BL6 mice. The enzyme β-hexosaminidase is one of several enzymes required for the catabolism of gangliosides, and its deficiency causes a storage disorder known as Sandhoff disease. A mouse model for Sandhoff disease (HEXB KO) that accumulates GA2 and GM2 gangliosides in neurons throughout the brain also accumulates pThr231-tau (a major component of NFTs) immunoreactivity, and deposits that are immunoreactive with antibodies against murine Aβ epitopes. pThr231-tau accumulation and increased sAPPβ and Aβ40 secretion in fibroblasts derived from patients with Sandhoff disease, indicate that defects in β-hexosaminidase activity can lead to alterations in APP processing both in vivo and in vitro.

The structure and metabolism of gangliosides in the brain can be found in Ariga, et al. ASBMB, 2008, 49:1157-1175.

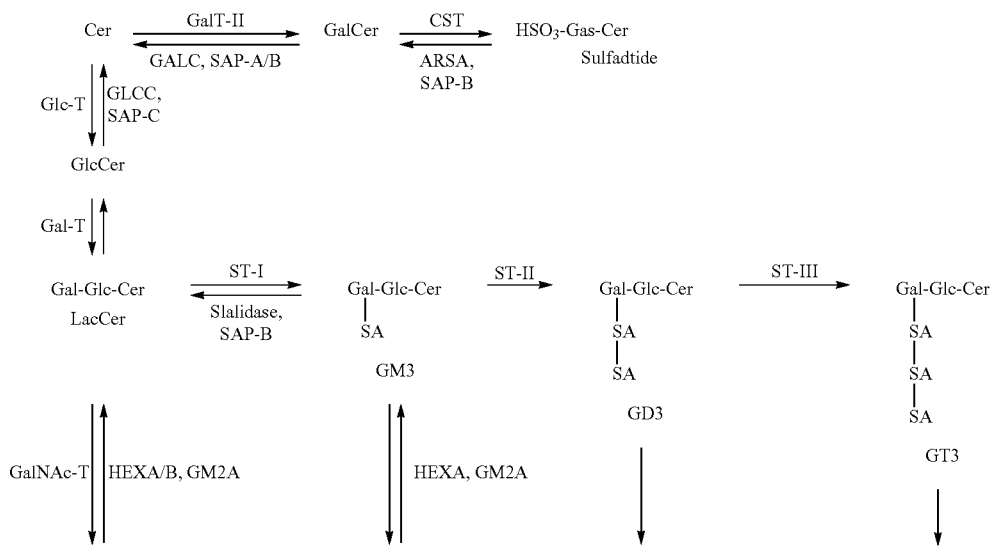

-continued

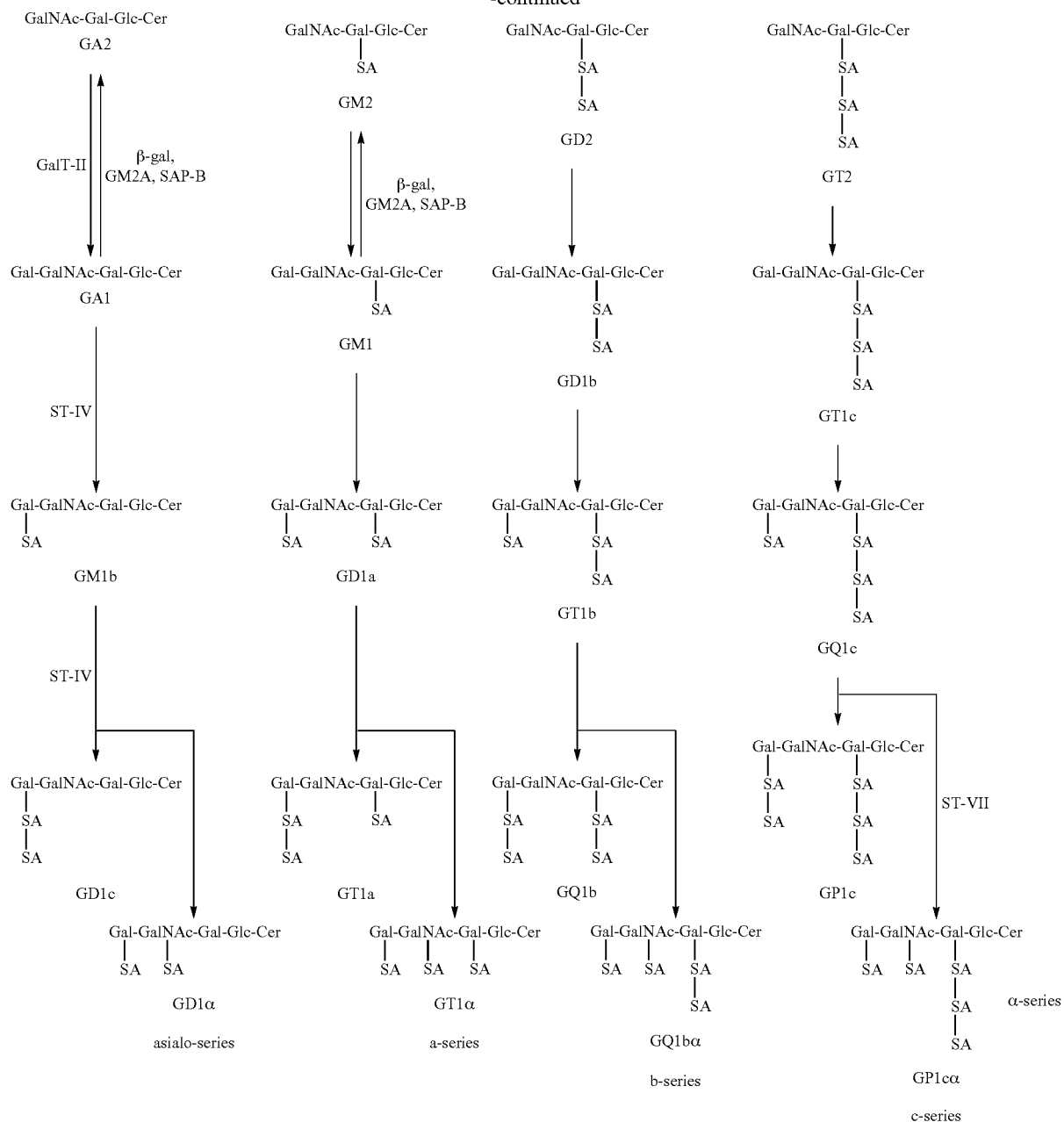

Definitions

The terms used in this specification generally have their ordinary meanings in the art, within the context of this invention and in the specific context where each term is used. Certain terms are discussed below, or elsewhere in the specification, to provide additional guidance to the practitioner in describing the invention and how to make and use the invention.

As used herein, the term "pharmacological chaperone," or sometimes "specific pharmacological chaperone" ("SPC"), refers to a molecule that specifically binds to one or more gangliosidases and/or sialidases, or glucocerebrosidase, and has one or more of the following effects: (i) enhancing the formation of a stable molecular conformation of the protein; (ii) enhances proper trafficking of the protein from the ER to another cellular location, preferably a native cellular location, i.e., preventing ER-associated degradation of the protein; (iii) preventing aggregation of conformationally unstable, i.e., misfolded proteins; (iv) restoring or enhancing at least partial wild-type function, stability, and/or activity of the protein; and/or (v) improving the phenotype or function of the cell. Thus, a pharmacological chaperone for gangliosidases or sialidases is a molecule that binds to one ore more gangliosidases and/or sialidases, resulting in proper folding, trafficking, non-aggregation, and increased activity of the gangliosidase and/or sialidase. It includes specific binding molecules, e.g., active site-specific chaperones, inhibitors, allosteric binders, non-active site binders that enhance protein stability. A pharmacological chaperon for glucocerebrosidase will have the same effect.

The term "Pharmacological chaperones" (PCs) refers to small molecules that selectively bind and stabilize target proteins to facilitate proper folding, reduce premature degradation and increase the efficiency of ER export. The small molecules are called "chaperones" because they help the proteins get from the where they are synthesized (the ER) to their intended location (e.g., the lysosome or the cell surface). The molecules are reversible binders which bind and stabilize the protein target, help restore proper trafficking, and then dissociate so the protein can carry out its proper function. The "pharmacological" modifier denotes molecular specificity: the molecules are designed to interact with and stabilize only a single intended protein target, and PCs do not generally affect multiple proteins or cellular processes such as protein trafficking, ER quality control, proteasome function, or the activity of biological chaperones (such as the heat shock proteins). This approach is broadly applicable to diseases where increasing the function of a specific protein (mutant or wild-type) is predicted to provide therapeutic benefit.

The retention and premature degradation of incorrectly folded proteins is not restricted to mutant proteins. It has been shown that a large fraction (up to 30%) of all newly synthesized proteins is targeted for premature degradation by the proteasomes. Subsequent studies have shown that pharmacological chaperones can increase cellular levels for many wild-type proteins by promoting protein folding, stability and ER export.

Molecular Chaperones Stabilize Protein Conformation.

In the human body, proteins are involved in almost every aspect of cellular function. Certain human diseases result from mutations that cause changes in the amino acid sequence of a protein which reduce its stability and may prevent it from folding properly. The majority of genetic mutations that lead to the production of less stable or misfolded proteins are called mis sense mutations. These mutations result in the substitution of a single amino acid for another in the protein. Because of this error, mis sense mutations often result in proteins that have a reduced level of biological activity. In addition to mis sense mutations, there are also other types of mutations that can result in proteins with reduced biological activity.

Proteins generally fold in a specific region of the cell known as the endoplasmic reticulum, or ER. The cell has quality control mechanisms that ensure that proteins are folded into their correct three-dimensional shape before they can move from the ER to the appropriate destination in the cell, a process generally referred to as protein trafficking. Misfolded and/or unstable proteins are often eliminated by the quality control mechanisms after initially being retained in the ER. In certain instances, misfolded proteins can accumulate in the ER before being eliminated.

The retention of misfolded proteins in the ER interrupts their proper trafficking, and the resulting reduced biological activity can lead to impaired cellular function and ultimately to disease. In addition, the accumulation of misfolded proteins in the ER may lead to various types of stress on cells, which may also contribute to cellular dysfunction and disease.

Endogenous molecular chaperones are present in virtually all types of cells and in most cellular compartments. Some are involved in the transport of proteins and permit cells to survive under stresses such as heat shock and glucose starvation. Among the endogenous chaperones (molecular chaperones), BiP (immunoglobulin heavy-chain binding protein, Grp78) is the best characterized chaperone of the ER Like other chaperones, BiP interacts with many secretory and membrane proteins within the ER throughout their maturation. When nascent protein folding proceeds smoothly, this interaction is normally weak and short-lived. Once the native protein conformation is achieved, the molecular chaperone no longer interacts with the protein. BiP binding to a protein that fails to fold, assemble, or be properly glycosylated becomes stable, and usually leads to degradation of the protein through the ER-associated degradation pathway. This process serves as a "quality control" system in the ER, ensuring that only those properly folded and assembled proteins are transported out of the ER for further maturation, and improperly folded proteins, or unstable proteins, are retained for subsequent degradation. Due to the combined actions of the inefficiency of the thermodynamic protein folding process and the ER quality control system, only a fraction of some wild-type proteins become folded into a stable conformation and successfully exit the ER.

Pharmacological Chaperones Derived from Specific Enzyme Inhibitors Rescue Mutant Enzymes and Enhance Wild-Type Enzymes.

The binding of small molecule inhibitors of enzymes associated with lysosomal storage diseases (LSDs), for instance, can increase the stability of both mutant enzyme and the corresponding wild-type enzyme (see U.S. Pat. Nos. 6,274,597; 6,583,158; 6,589,964; 6,599,919; 6,916,829, and 7,141,582 all incorporated herein by reference). In particular, it was discovered that administration of small molecule derivatives of glucose and galactose, which are specific, selective competitive inhibitors for several target lysosomal enzymes, effectively increased the stability of the enzymes in cells in vitro and, thus, increased trafficking of the enzymes to the lysosome. Thus, by increasing the amount of enzyme in the lysosome, hydrolysis of the enzyme substrates is expected to increase. Since the mutant enzyme protein is unstable in the ER, the enzyme protein is retarded in the normal transport pathway (ER→Golgi apparatus→endosomes→lysosome) and prematurely degraded. Therefore, certain compounds which binds to and increases the stability of a mutant enzyme, may serve as "chaperones" for the enzyme and increase the amount that can exit the ER and move to the lysosomes.

Since some enzyme inhibitors are known to bind specifically to the catalytic center of the enzyme (the "active site"), resulting in stabilization of enzyme conformation in vitro, these inhibitors were proposed, somewhat paradoxically, to be effective chaperones that could help restore exit from the ER, trafficking to the lysosomes, hydrolytic activity. These specific pharmacological chaperones were designated "active site-specific chaperones (ASSCs)" or "specific pharmacological chaperones" since they bound in the active site of the enzyme in a specific fashion. Pharmacological chaperone therapy has potential advantages over enzyme replacement therapy (ERT) since a small molecule can be orally administered and may have superior biodistribution compared to protein-based therapies.

In addition to rescuing the mutant enzymes, the pharmacological chaperones enhance ER secretion and activity of wild-type enzymes. Thus, a compound that induces a stable molecular conformation of an enzyme during folding serves as a "chaperone" to stabilize the enzyme in a proper conformation for exit from the ER. Pharmacological chaperones of gangliosidases and/or sialidases include, but are not limited to those provided in Tables 1 and 2. Additional guidance to terms used herein is provided below.

The term "ganglioside" or "sialoganglisides" refers to glycosphingolipids consisting of N-acylsphingosine and an oligosaccharide chain bearing one or more N-acetylneuraminic acid (sialic acid, NeuAc) residues.

The term "asialogangliosides" refers to gangliosides without N-acetylneuraminic acid (sialic acid, NeuAc) residues and include LacCer, GA2 and GA1 (Ariga et al.).

The term "gangliosidase" refers to sialidases and exoglycohydrolases which remove individual N-acetylneuraminic acid (sialic acid, NeuAc) and sugar residues sequentially from the non-reducing terminal unit of gangliosides and asialogangliosides. This degradation occurs mainly through the endocytosis-endosome-lysosome pathway. Examples of gangliosidases included sialidase 2 (neuraminidase 2; NEU2), sialidase 3 (neuraminidase 3; NEU3), sialidase 4 (neuraminidase 4; NEU4), β-galactosidase (GLB1), β-hexosaminidase A (HEXA/HEXB), β-hexosaminidase B (HEXB), and β-hexosaminidase S (HEXS).

The term "sialidases" refers to enzymes that remove individual N-acetylneuraminic acid (sialic acid, NeuAc) residues from the non-reducing terminal unit of gangliosides, oligosaccharides and glycoproteins. The term "sialidases" includes the enzymes sialidase 2 (neuraminidase 2), sialidase 3 (neuraminidase 3) and sialidase 4 (neuraminidase 4), which remove individual N-acetylneuraminic acid residues from gangliosides in the endosome-lysosome pathway, and sialidase 1, which removes individual N-acetylneuraminic acid residues from oligosaccharides and glycoproteins. N-acetylneuraminic acid residues on gangliosides have been shown to increase Aβ binding affinity and increase the tendency to induce β-sheet conformation. It was recently reported that knocking out disialoganglioside synthase (GD3S) in APP/PSEN mice (APPswe+PSEN1ΔE9) prevented both the accumulation of Aβ and the subsequent development of memory deficits that are characteristic of APP/PSEN mice. Bernardo, et al., Neurobiology of Aging. In Press, Corrected Proof, "Elimination of GD3 synthase improves memory and reduces amyloid-[beta] plaque load in transgenic mice." GD3S links sialic acid to sialic acid through an α-2,8-linkage and is required for the synthesis of b- and c-series gangliosides (Table 3). These results suggest that decreasing sialic acid content on gangliosides could be beneficial in treating AD.

The lysosomal enzyme "β-Galactosidase" is an exohydrolase that removes β1,3-galactose from the non-reducing end of asialo- and sialo-gangliosides. Mutations in the gene that encodes β-galactosidase, GLB1, causes the lysosomal storage disorder GM1 gangliosidosis, which results from a deficiency in β-galactosidase activity and the accumulation of GA1 and GM1 gangliosides. Beutler, E. et al., Biol. Chem. 247(22): 7195-200 (1972). GM1 ganglioside is a major component of the microdomains that promote the generation and assembly of Aβ in cell culture, and Aβ bound to GM1 (GAβ) has been found in brains exhibiting early stages of AD pathology.

The lysosomal enzymes β-Hexosaminidase A and B hydrolyze β-linked N-acetylgalactosamine (GalNAc) from the non-reducing end of asialo- and sialo-gangliosides. While GM1 gangliosides have received the most attention, other a-series gangliosides (GD1A, GM2 and GM3) also bind and promote the assembly of Aβ in vitro.

There are two isoenzymes of β-hexosaminidase, HEXA and HEXB. HEXA consists of a α-subunit and β-subunit (αβ), while HEXB consists of two β-subunits (ββ). HEXA encodes the α-subunit of HEXA and HEXB encodes the β-subunit of HEXA and HEXB. Mutations in HEXA causes the lysosomal storage disorder Tay-Sachs disease, which results from a deficiency in HEXA activity and the accumulation of GM2. Mutations in HEXB cause the lysosomal storage disorder Sandhoff disease, which results from a deficiency in HEXA and HEXB activities and the accumulation of GM2 and GA2.

Mice deficient in β-galactosidase activity (GLB1 KO) and β-hexosaminidase activity (HEXB KO) accumulate gangliosides in neurons throughout the brain. Accumulation of pThr231-tau immunoreactivity with a specific mAb, and deposits of material that are immunoreactive with antibodies against murine Aβ epitopes in the β-hexosaminidase deficient mice.

HEXB KO mice revealed the presence of amyloid-like deposits that immunoreacted with anti-rodent-Aβ. Similar immunoreactivity was observed through out the brains of NEU1 KO mice (Table 3), but no such Aβ-immunoreactive deposits were seen in the brains and spinal cords of age-matched wild-type control mice (Table 3). HEXB KO mice also demonstrated increased AT180 immunoreactivity, an antisera specific for tau that is phosphorylated at Thr231, through out the brain and spinal cord. No significant AT180 immunoreactivity was observed in the brain or spinal cord of age-matched wild-type mice. P(Thr231)-tau accumulation, decreased sAPPα, and increased sAPPβ and Aβ secretion was also observed in fibroblasts derived from patients with Sandhoff disease (FIG. 3), indicating that defects in β-hexosaminidase activity can lead to alterations in APP processing and tau phosphorylation both in vivo and in vitro.

Table 3. Primary and secondary accumulation of glycosphingolipids and proteins in the brains of mice deficient in neuraminidase 1 or β-hexosaminidase. No immunoreactivity was detected for age-matched controls.

TABLE 3

| mouse models | Secondary accumulation | | | Primary accumulation of enzyme substrates |
| --- | --- | --- | --- | --- |
| | α-synuclein | Aβ | p(Thr231)-tau | |
| neuraminidase 1 deficient (NEU1 −/−) | Yes | Yes | No | oligosaccharides with terminal sialic acid glycoproteins with terminal sialic acid |
| β-hexosaminidase A and B deficient (HEXB −/−) | Yes | Yes | Yes | GM2 gangliosides GA2 gangliosides oligosaccharides with terminal β-GlcNAc glycoproteins with terminal β-GlcNAc |

METHODS FOR GENERATION OF DATA SUMMARIZED IN TABLE 3: Brains from 4 month old HEXB −/− mice and age-matched controls were embedded in paraffin blocks and coronally cut in series with 5 µm slice thickness. Four month old NEU1−/− and age-matched control mice were transcardially perfused with physiological (0.9%) saline and brains were rapidly removed and hemisected. The right hemispheres of all mice were immersion fixed in freshly produced 4% Paraformaldehyde/PBS (pH 7.4) for one hour at room temperature. Brains were then transferred into a 15% sucrose in PBS solution for 24 hours to ensure cryoprotection. On the next day brains were frozen in liquid Isopentane and stored at −80° C. until used for histological investigations. The right hemisphere was chosen for histological investigations and five slices per brain hemisphere deriving from five different sagittal layers were cryo-cut and immunohistochemically stained. Amyloid- and pThr231-tau-like immunoreactivity was qualitatively assessed after IHC using anti-rodent-Aβ (Abcam®, ab14220) or anti-pThr231-tau (Thermo Scientific, AT180) (developed with HistoGreen (Linaris®). Rodent amyloid detection slices were pretreated with citrate buffer for 15 minutes at 95° C. in a steamer to demask antigen, then incubated with a polyclonal rabbit anti beta-amyloid primary (Abcam®, ab14220) at 1:500 for one hour at room temperature and consequently targeted with a biotinylated rabbit IgG detection antibody followed by a HistoGreen (Linaris®) development. For detection of PHF-TAU (AT180) paraffin slices were pretreated with citrate buffer for 15 minutes at 95° C. in a steamer to demask antigen, then incubated with an Anti-Human PHF-Tau monoclonal antibody (1:100 diluted in MOM-Diluent; Pierce Endogen®, Cat. No. MN1040) for one hour at room temperature and consequently targeted with a biotinylated mouse IgG detection antibody followed by a HistoGreen (Linaris®) development. In cryo-cut slices pre-treatment with citrate buffer was omitted.

TABLE 4

Comparative Selectivity of Pharmacological Chaperones

| Target | NB-DANA Neu 1 | DANA Neu 1-4 | Phenyl DANA Neu 1 | NGT Hex A/B | pyrimeth-amine Hex A/B | AdDNJ Hex A/B | Zan-amivir Neu 3 |
|---|---|---|---|---|---|---|---|
| IC50 | | | | | | | |
| B-Hex | | | | .3** | 13* | .7** | |
| Neu 1 | 10 | 143* | 13* | | | | 2713* |
| Neu 2 | >1000* | 43* | 865* | | | | 16* |
| Neu 3 | >1000* | 61* | 320* | | | | 7* |
| Neu 4 | >1000* | 74* | 810* | | | | 690* |

*Values reported in the literature
**Values reported as Ki's

As used herein, the term "specifically binds" refers to the interaction of a pharmacological chaperone with gangliosidases and/or sialidases, or glucocerebrosidase, specifically, an interaction with amino acid residues of a gangliosidases and/or a sialidases, or glucocerebrosidase, that directly participate in contacting the pharmacological chaperone. A pharmacological chaperone specifically binds a target protein, e.g., β-hexosaminidase B, to exert a chaperone effect on the enzyme and not a generic group of related or unrelated proteins. The amino acid residues of β-hexosaminidase that interact with any given pharmacological chaperone may or may not be within the protein's "active site." Specific binding can be evaluated through routine binding assays (e.g. inhibition, thermal stability) or through structural studies, e.g., co-crystallization, NMR, and the like.

As used herein, the terms "enhance stability" or "increase stability" refers to increasing an enzymes resistance to irreversible inactivation in vitro or in a cell contacted with a pharmacological chaperone specific for a gangliosidases and/or sialidases, or for glucocerebrosidase, relative to gangliosidases and/or sialidases (preferably of the same cell-type or the same cell, e.g., at an earlier time), or for glucocerebrosidase, that are not contacted with the pharmacological chaperone. Increasing protein stability increases the half-life of the protein in the ER and the amount of functional protein trafficked from the ER. In one aspect of the invention the stability of a wild type gangliosidase or sialidase, or glucocerebrosidase, is enhanced or increased. In another aspect of the invention the conformational stability of a mutant gangliosidase or sialidase or glucocerebrosidase is enhanced or increased.

As used herein, the terms "enhance trafficking" or "increase trafficking" refer to increasing the efficiency of the transport of a gangliosidase and/or sialidase or glucocerebrosidase to the cytosol (sialidase 2) or the endosomes and lysosomes of a cell contacted with a pharmacological chaperone specific to one ore more gangliosidases and/or sialidases or glucocerebrosidase, relative to the efficiency of transport of a gangliosidase and/or a sialidase or glucocerebrosidase in a cell (preferably of the same cell-type or the same cell, e.g., at an earlier time) not contacted with the pharmacological chaperone specific for a gangliosidase and/or a sialidase or glucocerebrosidase.

As used herein, the terms "enhance activity" or "increase activity" refer to increasing the activity of gangliosidases and/or sialidases or glucocerebrosidase, as described herein, in a cell contacted with a pharmacological chaperone specific for one or more gangliosidases and/or sialidases or glucocerebrosidase, relative to the activity of gangliosidases and/or sialidases or glucocerebrosidase in a cell (preferably of the same cell-type or the same cell, e.g., at an earlier time) not contacted with the pharmacological chaperone specific for one or more gangliosidases and/or sialidases or glucocerebrosidase. Pharmacological chaperones of the present invention may also increase enzyme activity by increasing the total amount of enzyme in the cell and/or by increasing an enzyme's specific activity.

The term "specific activity" refers to the amount of substrate an enzyme converts per milligram of protein in an enzyme preparation, per unit of time.

As used herein, the terms "enhance level" or "increase level" refer to increasing the level of one or more gangliosidases and/or sialidases or glucocerebrosidase in a cell contacted with a pharmacological chaperone specific for one or more gangliosidases and/or sialidases or glucocerebrosidase, relative to the level of gangliosidases and/or sialidases or glucocerebrosidase in a cell (preferably of the same cell-type or the same cell, e.g., at an earlier time) not contacted with the pharmacological chaperone specific for one or more gangliosidases and/or sialidases or glucocerebrosidase.

The term "stabilize a proper conformation" refers to the ability of a gangliosidase and/or a sialidase or glucocerebrosidase pharmacological chaperone to induce or stabilize a conformation of a mutated or wild type gangliosidase and/or sialidase or glucocerebrosidase enzyme that is functionally identical to the conformation of the wild-type gangliosidase and/or sialidase or glucocerebrosidase that performs its intended function.

The term "functionally identical" means that while there may be minor variations in the conformation (almost all proteins exhibit some conformational flexibility in their physiological state), conformational flexibility does not result in (1) protein aggregation, (2) elimination through the endoplasmic reticulum-associated degradation pathway, (3) impairment of protein function, e.g., APP metabolic activity, and/or (4) improper transport within the cell, e.g., localization to the cytosol, to a greater or lesser degree than that of the wild-type protein.

The term "stable molecular conformation" refers to a conformation of a protein, i.e., a gangliosidase and/or sialidase or glucocerebrosidase, induced by a pharmacological chaperone that provides at least partial wild-type function in the cell or to enhance wild-type function. For example, a stable molecular conformation of a gangliosidase and/or sialidase or glucocerebrosidase would be one where the gangliosidase and/or sialidase or glucocerebrosidase leaves the ER and traffics to the cytosol, instead of misfolding and being degraded and/or not performing its intended function. In addition, a stable molecular conformation of a mutated gangliosidase and/or sialidase or glucocerebrosidase may also possess full or partial activity. However, it is not necessary that the stable molecular conformation have all of the functional attributes of the wild-type protein.

The term "activity" refers to the normal intended physiological function of a wild-type gangliosidase and/or sialidase or glucocerebrosidase in a cell. For example, gangliosidase and/or sialidase activity includes catabolism of gangliosides and glucocerebrosidase activity includes catabolism of the glycosphingolipid glucosylceramide. Such functionality can be tested by any means known to establish functionality.

The term "ganglioside catabolism" refers to the removal of individual sialic acid and sugar residues sequentially from the non-reducing terminal unit of asialo- and sialo-gangliosides by sialidases and exoglycohydrolases with the formation of ceramide. This degradation occurs mainly through the endocytosis-endosome-lysosome pathway with the exception of sialidase 2, which is located in the cytosol.

In one non-limiting embodiment, a gangliosidase and/or sialidase, or glucocerebrosidase polypeptide may be encoded for by any nucleic acid molecule exhibiting 50%, 60%, 70%, 80% and up to 100% homology to the nucleic acid molecules encoding a wild type gangliosidase and/or a sialidase or glucocerebrosidase, and any sequences which hybridize under standard conditions to these sequences. In another non-limiting embodiment, any other nucleotide sequence that encodes a gangliosidase and/or a sialidase or a glucocerebrosidase polypeptide (having the same functional properties and binding affinities as the aforementioned polypeptide sequences), such as allelic variants in normal individuals, that have the ability to achieve a functional conformation in the ER, achieve proper localization within the cell, and exhibit wild-type activity.

As used herein the term "mutant" gangliosidase and/or a sialidase or glucocerebrosidase refers to a gangliosidase and/or a sialidase or glucocerebrosidase polypeptide translated from a gene containing a genetic mutation that results in an altered gangliosidase and/or a sialidase or glucocerebrosidase amino acid sequence. In one embodiment, the mutation results in a gangliosidase and/or a sialidase or glucocerebrosidase protein that does not achieve a native conformation under the conditions normally present in the ER, when compared with wild-type gangliosidase and/or a sialidase or glucocerebrosidase, or exhibits decreased stability or activity as compared with a wild-type gangliosidase and/or sialidase or glucocerebrosidase. This type of mutation is referred to herein as a "conformational mutation," and the protein bearing such a mutation is referred as a "conformational mutant." The failure to achieve this conformation results in a gangliosidase and/or a sialidase or glucocerebrosidase protein being degraded or aggregated, rather than being transported through a normal pathway in the protein transport system to its native location in the cell or into the extracellular environment. In some embodiments, a mutation may occur in a non-coding part of the gene encoding a gangliosidase and/or a sialidase or glucocerebrosidase that results in less efficient expression of the protein, e.g., a mutation that affects transcription efficiency, splicing efficiency, mRNA stability, and the like. By enhancing the level of expression of wild-type as well as conformational mutant variants of a gangliosidase and/or a sialidase or glucocerebrosidase, administration of a gangliosidase and/or a sialidase or glucocerebrosidase pharmacological chaperone can ameliorate a deficit resulting from such inefficient protein expression.

Certain tests may evaluate attributes of a protein that may or may not correspond to its actual in vivo activity, but nevertheless are appropriate surrogates of protein functionality, and wild-type behavior in such tests demonstrates evidence to support the protein folding rescue or enhancement techniques of the invention. One such activity in accordance with the invention is appropriate transport of a functional a gangliosidase and/or a sialidase from the endoplasmic reticulum to the cytosol.

The terms "endogenous expression" and "endogenously expressed" refers to the normal physiological expression of a gangliosidase and/or a sialidase or glucocerebrosidase in cells in an individual not having or suspected of having a disease or disorder associated with gangliosidase and/or sialidase or glucocerebrosidase deficiency, overexpression of a dominant negative mutant, or other defect, such as a mutation in a gangliosidase and/or a sialidase or glucocerebrosidase nucleic acid or polypeptide sequence that alters, e.g., inhibits, its expression, activity, or stability. This term also refers to the expression of a gangliosidase and/or a sialidase or glucocerebrosidase in cells or cell types in which it is normally expressed in healthy individuals, and does not include expression of a gangliosidase and/or a sialidase or glucocerebrosidase in cells or cell types, e.g., tumor cells, in which a gangliosidase and/or a sialidase or glucocerebrosidase is not expressed in healthy individuals.

As used herein, the term "elevated ganglioside" refers to an individual, patient or patient population having increased ganglioside levels in the brain. The ganglioside levels may be elevated in the membranes through out the cell and also within microdomains. The term "microdomains" or "lipid rafts" refers to detergent resistant areas found within cell membranes that are enriched in cholesterol, glycosphingolipids and gangliosides. In on aspect of this invention, pharmacological chaperones are used to decrease ganglioside levels in microdomains or lipid rafts by increasing the activity of enzymes known to catabolize gangliosides in the brain.

As used herein, the term "efficiency of transport" refers to the ability of a protein to be transported out of the endoplasmic reticulum to its native location within the cell, cell membrane, or into the extracellular environment.

A "competitive inhibitor" of an enzyme can refer to a compound which structurally resembles the chemical structure and molecular geometry of the enzyme substrate to bind the enzyme in approximately the same location as the substrate. Thus, the inhibitor competes for the same active site as the substrate molecule, thus increasing the Km. Competitive inhibition is usually reversible if sufficient substrate molecules are available to displace the inhibitor, i.e., competitive inhibitors can bind reversibly. Therefore, the amount of enzyme inhibition depends upon the inhibitor concentration, substrate concentration, and the relative affinities of the inhibitor and substrate for the active site.

Non-classical competitive inhibition occurs when the inhibitor binds remotely to the active site of an enzyme, creating a conformational change in the enzyme such that the substrate can no longer bind to it. In non-classical competitive inhibition, the binding of substrate at the active site prevents the binding of inhibitor at a separate site and vice versa. This includes allosteric inhibition.

A "linear mixed-type inhibitor" of an enzyme is a type of competitive inhibitor that allows the substrate to bind, but reduces its affinity, so the Km is increased and the Vmax is decreased.

A "non-competitive inhibitor" refers to a compound that forms strong bonds with an enzyme and may not be displaced by the addition of excess substrate, i.e., non-competitive inhibitors may be irreversible. A non-competitive inhibitor may bind at, near, or remote from the active site of an enzyme or protein, and in connection with enzymes, has no effect on the Km but decreases the Vmax. Uncompetitive inhibition refers to a situation in which inhibitor binds only to the enzyme-substrate (ES) complex. The enzyme becomes inactive when inhibitor binds. This differs from non-classical competitive inhibitors which can bind to the enzyme in the absence of substrate.

The term "Vmax" refers to the maximum initial velocity of an enzyme catalyzed reaction, i.e., at saturating substrate levels. The term "Km" is the substrate concentration required to achieve ½ Vmax.

An enzyme "enhancer" is a compound that binds to a gangliosidase and/or a sialidase and increases the enzymatic reaction rate.

The terms "therapeutically effective dose" and "effective amount" refer to an amount sufficient to enhance protein processing in the ER (permitting a functional conformation), without inhibiting protein already expressed at the appropriate cellular location (in the case of an antagonist), or without inducing ligand-mediated receptor internalization of protein from the appropriate cellular location (in the case of an agonist), and enhance activity of the target protein, thus resulting in a therapeutic response in a subject. A therapeutic response may be any response that a user (e.g., a clinician) will recognize as an effective response to the therapy, including the foregoing symptoms and surrogate clinical markers. Thus, a therapeutic response will generally be an amelioration or inhibition of one or more symptoms of a disease or disorder, e.g., Alzheimer's Disease.

The phrase "pharmaceutically acceptable" refers to molecular entities and compositions that are physiologically tolerable and do not typically produce untoward reactions when administered to a human. Preferably, as used herein, the term "pharmaceutically acceptable" means approved by a regulatory agency of the federal or a state government or listed in the U.S. Pharmacopeia or other generally recognized pharmacopeia for use in animals, and more particularly in humans. The term "carrier" refers to a diluent, adjuvant, excipient, or any vehicle with which the compound is administered. Such pharmaceutical carriers, for example, can be sterile liquids, such as water and oils. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition, or other editions.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

As used herein, the term "isolated" means that the referenced material is removed from the environment in which it is normally found. Thus, an isolated biological material can be free of cellular components, i.e., components of the cells in which the material is found or produced. In the case of nucleic acid molecules, an isolated nucleic acid includes a PCR product, an mRNA band on a gel, a cDNA, or a restriction fragment. In another embodiment, an isolated nucleic acid is preferably excised from the chromosome in which it may be found, and more preferably is no longer joined to non-regulatory, non-coding regions, or to other genes, located upstream or downstream of the gene contained by the isolated nucleic acid molecule when found in the chromosome. In yet another embodiment, the isolated nucleic acid lacks one or more introns. Isolated nucleic acids include sequences inserted into plasmids, cosmids, artificial chromosomes, and the like. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The term "purified" as used herein refers to material, such as a gangliosidase and/or a sialidase nucleic acid or polypeptide that has been isolated under conditions that reduce or eliminate unrelated materials, i.e., contaminants. For example, a purified protein is preferably substantially free of other proteins or nucleic acids with which it is associated in a cell. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by conventional means, e.g., chromatography, gel electrophoresis, immunoassay, composition analysis, biological assay, and other methods known in the art.

The term "Tauopathy" refers to any condition resulting from the pathological aggregation of tau protein forming neurofibrillary tangles (NFT) in the human brain and includes (but is not limited to) diseases such as Frontotemporal dementia, Alzheimer's disease, Progressive supranuclear palsy, Corticobasal degenerations and frontotemporal lobar degeneration (Pick's disease).

The term "Alzheimer's Disease" or "AD" refers to a condition characterized by slowly progressive dementia and gross cerebral cortical atrophy. The presence of β-amyloid neuritic plaques, intra neuronal neurofibrillary tangles, and amyloid angiopathy are hallmarks of AD and are observed at postmortem examination. AD may be heritable in a Familial manifestation, or may be sporadic. Herein, AD includes Familial, Sporadic, as well as intermediates and subgroups thereof based on phenotypic manifestations. Familial AD typically has an early-onset (before age 65) while Sporadic AD typically is late-onset (age 65 and later).

In a non-limiting embodiment, Familial AD may be associated with mutations in one or more genes selected from the group comprising presenilin 1 (human presenilin 1, GenBank Accession Nos. NM_000021, NM_007318, and NM_007319; murine presenilin 1, GenBank Accession No. NM_008943; and rat presenilin 1, GenBank Accession No. NM_019163), presenilin 2 (human presenilin 2, GenBank Accession Nos. NM_000447, and NM_012486; murine presenilin 2, GenBank Accession No. NM_011183; and rat presenilin 2, GenBank Accession No. NM_031087), and Amyloid Precursor Protein (APP) (human APP, GenBank Accession Nos. NM_201414, NM_201413, and NM_000484; murine APP, GenBank Accession No. NM_007471; and rat APP, GenBank Accession No. NM_019288). Sporadic AD can not be tested for directly, but certain risk factors may increase an individual's susceptibility to developing sporadic AD. In one, non-limiting embodiment, individuals with at least one copy of the e4 allele of Apolipoprotein E (APOE) (human APOE, GenBank Accession No. NM_000041; murine APOE, GenBank Accession No. NM_009696; and rat APOE, GenBank Accession No. NM_138828) are at risk of developing late-onset sporadic AD.

This term also includes individuals with trisomy 21, or Down syndrome (DS), develop dementia that is identical to the clinical and neurophathogic characteristics of AD (in their third or fourth decade), including cerebral amyloid (A$\beta$) plaques and neurofibrillary tangles (NFTs), the characteristic lesions of Alzheimer disease (AD). Recent studies have shown that the A$\beta$42 is the earliest form of this protein deposited in Down syndrome brains, and may be seen in subjects as young as 12 years of age, and that soluble A$\beta$ can be detected in the brains of DS subjects as early as 21 gestational weeks of age, well preceding the formation of A$\beta$ plaques. Gyure et al., Archives of Pathology and Laboratory Medicine 125: 489-492 (2000).

For purposes of the present invention, a "neurological disorder" refers to any central nervous system (CNS) or peripheral nervous system (PNS) disease that is associated with the $\beta$-amyloidogenic processing of Amyloid Precursor Protein. This may result in neuronal or glial cell defects including but not limited to neuronal loss, neuronal degeneration, neuronal demyelination, gliosis (i.e., astrogliosis), or neuronal or extraneuronal accumulation of aberrant proteins or toxins (e.g., amyloid-$\beta$).

One exemplary neurological disorder is cerebral amyloid angiopath (CAA) also referred to as congophilic angiopathy. This disorder is a form of angiopathy in which the same amyloid protein that is associated with Alzheimer's disease, amyloid-$\beta$ (A$\beta$), deposits in the walls of the leptomeninges and superficial cerebral cortical blood vessels of the brain. Amyloid deposition predisposes these blood vessels to failure, increasing the risk of a hemorrhagic stroke. Since it is the same amyloid protein that is associated with Alzheimer's dementia, such brain hemorrhages are more common in people who suffer from Alzheimer's, however they can also occur in those who have no history of dementia. The hemorrhage within the brain is usually confined to a particular lobe and this is slightly different compared to brain hemorrhages which occur as a consequence of high blood pressure (hypertension)—a more common cause of a hemorrhagic stroke (or cerebral hemorrhage). CAA is also associated with transient ischemic attacks, subarachnoid hemorrhage, Down syndrome, post irradiation necrosis, multiple sclerosis, leucoencephalopathy, spongiform encephalopathy, and dementia pugilistica.

The term "individual" "patient" or "patient population" refers to a person(s) diagnosed as having Alzheimer's Disease or at risk of developing Alzheimer's Disease. For instance, the individuals are diagnosed, or at risk of developing Familial AD. In another instance, the individual is diagnosed as having, or at risk of developing, Sporadic AD. Diagnosis of AD may be made based on genotypic or phenotypic characteristics displayed by the individual. For example, an individual with a mutant variant of presenilin 1, presenilin 2, or APP are at risk of developing familial AD. In another, non-limiting example, individuals with the E4 variant of APOE are at risk for developing Sporadic AD.

An individual may be diagnosed as having AD, or at risk of developing AD, by exhibiting phenotypes associated with AD. Phenotypes associated with AD may be cognitive or psychiatric. Examples of cognitive phenotypes include, but are not limited to, amnesia, aphasia, apraxia and agnosia. Examples of psychiatric symptoms include, but are not limited to, personality changes, depression, hallucinations and delusions. As one non-limiting example, the Diagnostic and Statistical Manual of Mental disorders, 4th Edition (DSM-W-TR) (published by the American Psychiatric Association) contains the following set of criteria for dementia of the Alzheimer's type:

A. The development of multiple cognitive deficits manifested by both memory impairment and one or more of Aphasia, Apraxia, Agnosia and disturbances in executive functioning;

B. The cognitive deficits represent as decline from previous functioning and cause significant impairment in social or occupational functioning;

C. The course is characterized by gradual onset and continuing decline;

D. The cognitive deficits are not due to other central nervous system, systemic, or substance-induced conditions that cause progressive deficits in memory and cognition; and E. The disturbance is not better accounted for by another psychiatric disorder.

Another non-limiting example is The National Institute of Neurological and Communicative Disorders and Stroke-Alzheimer's Disease and Related Disorder Association (NINDS-ADRDA) Criteria for Alzheimer's Disease as follows:

A. Definite Alzheimer's disease: meets the criteria for probable Alzheimer's disease and has histopathologic evidence of Alzheimer's disease via autopsy or biopsy B. Probable Alzheimer's disease: dementia established by clinical and neuropsychological examination and involves
    (a) progressive deficits in two or more areas of cognition, including memory,
    (b) onset between the ages of 40 and 90 years, and
    (c) absence of systemic or other brain diseases capable of producing a dementia syndrome, including delirium C. Possible Alzheimer's disease: a dementia syndrome with an atypical onset, presentation, or progression and without a known etiology; any co-morbid diseases capable of producing dementia are not believed to be the cause D. Unlikely Alzheimer's disease: a dementia syndrome with any of the following: sudden onset, focal neurologic signs, or seizures or gait disturbance early in the course of the illness.

Phenotypic manifestations of AD may also be physical, such as by the direct (imaging) or indirect (biochemical) detection of amyloid-$\beta$ plaques. Quantitation of amyloid-$\beta$ (1-40) in the peripheral blood has been demonstrated using high-performance liquid chromatography coupled with tandem mass spectrometry in a linear ion trap (Du et al., J Biomol Tech. 16(4):356-63 (2005). Detection of single β-amyloid protein aggregates in the cerebrospinal fluid of Alzheimer's patients by fluorescence correlation spectroscopy also has been described (Pitschke et al., Nature Medicine 4: 832-834 (1998). U.S. Pat. No. 5,593,846 describes a method for detecting soluble amyloid-β. Indirect detection of amyloid-β peptide and receptor for advanced glycation end products (RAGE) using antibodies also has been described. Lastly, biochemical detection of increased BACE-1 activity in cerebrospinal fluid using chromogenic substrates also has been postulated as a diagnostic or prognostic indicator of AD (Verheijen et al., Clin Chem. April 13 [Epub.] (2006).

In vivo imaging of β-amyloid can be achieved using radioiodinated flavone derivatives as imaging agents, Ono et al., J Med Chem. 48(23):7253-60 (2005), and with amyloid binding dyes such as putrescein conjugated to a 40-residue radioiodinated A peptide (yielding $^{125}$I-PUT-A 1-40), which was shown to cross the blood-brain barrier and bind to αβ plaques. Wengenack et al., Nature Biotechnology. 18(8): 868-72 (2000). Imaging of β-amyloid was also shown using stilbene SB-13 and the benzothiazole 6-OH-BTA-1 (also known as PIB). Nicholaas et al., Am J Geriatr Psychiatry, 12:584-595 (2004).

EXAMPLES

FIG. 1 represents the processing of APP and shows how mature APP is metabolized by 2 competing pathways, the α-secretase pathway that generates sAPPα and C83 (left) and the β-secretase pathway that generates sAPPβ and C99 (right). Carboxy terminal fragments C83 and C99 are substrates for γ-secretase, generating the APP intracellular domain (AICD) and the secreted peptides p3 (left) and Aβ (right). Aβ peptides can oligomerize, form plaques and promote tau hyperphosphorylation, while sAPPα promotes neurite outgrowth, synaptogenesis and suppresses tau hyperphosphorylation associated with CDK5 activation.

The data shown in FIG. 2 was generated as follows. Brain tissue from HEXB +/+ mice (~4.5 months old), HEXB+/− mice (~4.5 months old) and HEXB−/− mice (~4.5 months old) was minced and mixed with 10× volume (1 ml/100 mg tissue) of cold tissue homogenization buffer (THB: 250 mM sucrose, 50 mM Tris pH 7.5, 1 mM EDTA plus protease inhibitors). The brain tissue was then homogenized using a rotor stator homogenizer. The brain homogenate was transferred into a clean ultra centrifuge tube, placed in a pre-chilled RP70-AT rotor and centrifuged at 50,000 rpm (~100,000 g) for 1 hr at 4° C. The soluble fraction (supernatant) was used for determining the levels of sAPP by immunoblotting using the 22C11 antibody (Millipore). For measurement of Aβ40 and Aβ42 levels, the soluble fraction (supernatant) was extracted with diethylamine (DEA). The DEA homogenate was centrifuged at 50,000 rpm (~100,000 g) for 1 hr at 4° C., and the supernatant was neutralized by adding 0.1× volume of 0.5M Tris pH 7. The neutralized DEA extract was then used for measurement of Aβ40 and Aβ42 levels by ELISA kits (Wako). To obtain the membrane fraction, RIPA buffer (1% TX100, 0.5% Taurodeoxycholate, and 0.1% SDS in TBS plus protease inhibitors) was added to the membrane pellet in the ultracentrifuge tube. The membranes were solubilized in the RIPA buffer by incubation on ice for 30 min. RIPA-solubilized membranes were obtained by centrifugation at 25,000 rpm for 15 min at 4° C. The membrane fractions were immunoblotted using polyclonal APP-CT antibody (Covance) to determine the levels of APP, α-CTF and β-CTF. For analysis of tau levels, membrane fractions were prepared as described above, and were immunoblotted using AT180 antibody (Thermo Scientific) to determine the levels of p-Tau (Thr231), AT8 antibody (Thermo Scientific) to determine the levels of p-Tau (Ser 202), total tau antibody (Thermo Scientific) to determine the levels of total tau. The level of p-Tau (Thr181) in the membrane fractions was determined by performing an ELISA (Invitrogen) assay according to the manufacturer's recommended protocol. For histological analyses, cortex from the Brain from a HEXB KO mice was embedded in paraffin blocks. Amyloid- and pThr231-tau-like immunoreactivity was qualitatively assessed after IHC using antibody FC3542 (Calbiochem) that specifically recognizes Aβ42 or using AT8 antibody (Thermo Scientific) that specifically recognizes p-Tau (Thr202).

Figure 2:
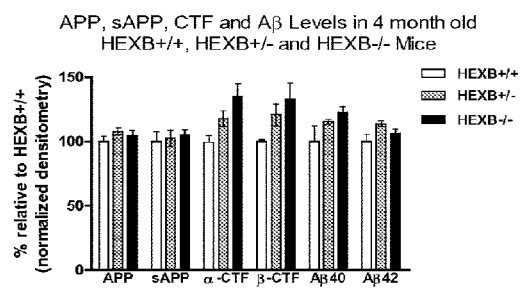
FIG. 2 shows evidence of altered APP metabolism and tau phosphorylation in the brains of mice deficient in β-hexosaminidase activity.
Figure 2:
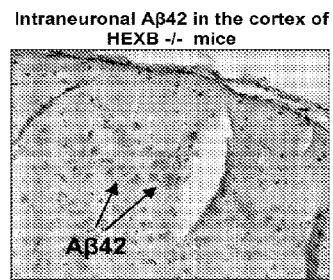
Figure 2:
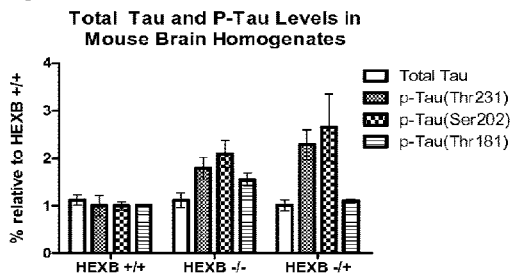
Figure 2:
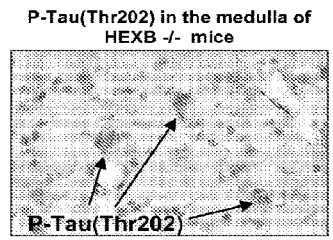

As shown in FIG. 2, Sandhoff HEXB knock-out mice (HEXB −/−) and Sandhoff HEXB heterozygous mice (HEXB+/−) accumulate amyloid precursor protein (APP) derived C-terminal fragments (CTF) and Aβ peptides and have increased levels of phosphorylated tau. FIG. 2A) represents normalized densitometry of western blots show increased CTF and Aβ levels in total brain homogenates from 4 month old HEXB −/− and HEXB+/− mice (n=4). FIG. 2B) shows histological analysis shows accumulation of intraneuronal A (342 in cortex of HEXB−/− mice. FIG. 2C) represents ELISA (p-Tau[Thr181]) and normalized densitometry of western blots (p-Tau[Thr231] and p-Tau[Ser202], total tau) show elevated levels of p-Tau in HEXB−/− and HEXB+/− mice relative to age-matched HEXB+/+ mice, but no significant differences in total tau levels. FIG. 2D) shows histological analysis shows accumulation of p-Tau(202) in the medulla and spinal cord (data not shown) of HEXB−/− mice.

The data shown in FIG. 3 was generated as follows. A wild type (healthy) fibroblast cell line (CRL2076; Coriell) and a fibroblast cell line from a Sandhoff patient (GM11707; Coriell) were cultured overnight in DMEM (plus 10% FBS) growth medium, followed by an overnight incubation in serum free media. Secreted proteins were collected by TCA precipitation (12.5%) of the growth media and analyzed by immunoblotting using 6E10 antibody (Covance) to determine the levels of sAPPα. To determine the levels of secreted sAPPβ, fibroblasts (CRL2076 & GM11707) were cultured in DMEM (plus 10% FBS) growth medium for 5 days, followed by immunoprecipitation using a biotinylated monoclonal antibody against APP (1G6; Covance), and western blotting using an affinity purified polyclonal antibody against sAPPβ (Covance). To measure levels of secreted Aβ40 in media, fibroblasts (CRL2076 & GM11707) were cultured overnight in DMEM (plus 10% FBS) growth medium (3 wells/sample; 1 ml media/well), followed by an overnight incubation in serum free media. The 3 wells/sample were combined and mixed with 0.3 ml methanol, 30 μl 10% TFA (Trifluoroacetic acid). The samples were pre-concentrated using a Sepak C18 column (Waters) and then used in an ELISA assay (Covance) to determine the levels of Aβ40. To determine the levels of full length APP, fibroblasts (CRL2076 & GM11707) were cultured overnight in DMEM (plus 10% FBS) growth medium. The cells were scraped, harvested by centrifugation, and the cell pellet was solubilized using RIPA buffer (1% TX100, 0.5% Taurodeoxycholate, and 0.1% SDS in TBS plus protease inhibitors). The cell lysate was immunoblotted using the APP-CT antibody (Covance) to determine the levels of full length APP. To determine the levels of ADAM10, fibroblasts (CRL2076 & GM11707) were cultured overnight in DMEM (plus 10% FBS) growth medium. The cells were scraped, harvested by centrifugation, and the cell pellet was solubilized using RIPA buffer (1% TX100, 0.5% Taurodeoxycholate, and 0.1% SDS in TBS plus protease inhibitors). The cell lysate was immunoblotted using a rabbit polyclonal antibody specific for ADAM10 (Abcam). To determine the levels of BACE1, fibroblasts (CRL2076 & GM11707) were cultured overnight in DMEM (plus 10% FBS) growth medium. The cells were scraped, harvested by centrifugation, and the cell pellet was solubilized using RIPA buffer (1% TX100, 0.5% Taurodeoxycholate, and 0.1% SDS in TBS plus protease inhibitors). The cell lysate was immunoblotted using a rabbit polyclonal antibody specific for BACE1 (Abcam). To determine the levels of pThr231-tau, fibroblasts (CRL2076 & GM11707) were cultured overnight in DMEM (plus 10% FBS) growth medium. The cells were scraped, harvested by centrifugation, and the cell pellet was solubilized using RIPA buffer (1% TX100, 0.5% Taurodeoxycholate, and 0.1% SDS in TBS plus protease inhibitors). The cell lysate was immunoblotted using a mouse monoclonal antibody specific for pThr231-tau (AT180; Thermo Scientific). Healthy fibroblasts (CRL2076; Coriell) were treated with 0, 100 or 1000 μM N-butyl-deoxygalactonojirimycin (NB-DGJ) for 5 days, followed by an overnight incubation in serum free media. Secreted proteins were collected by TCA precipitation (12.5%) of the growth media and analyzed by immunoblotting using 6E10 antibody (Covance) to determine the levels of sAPPα.

Figure 3:
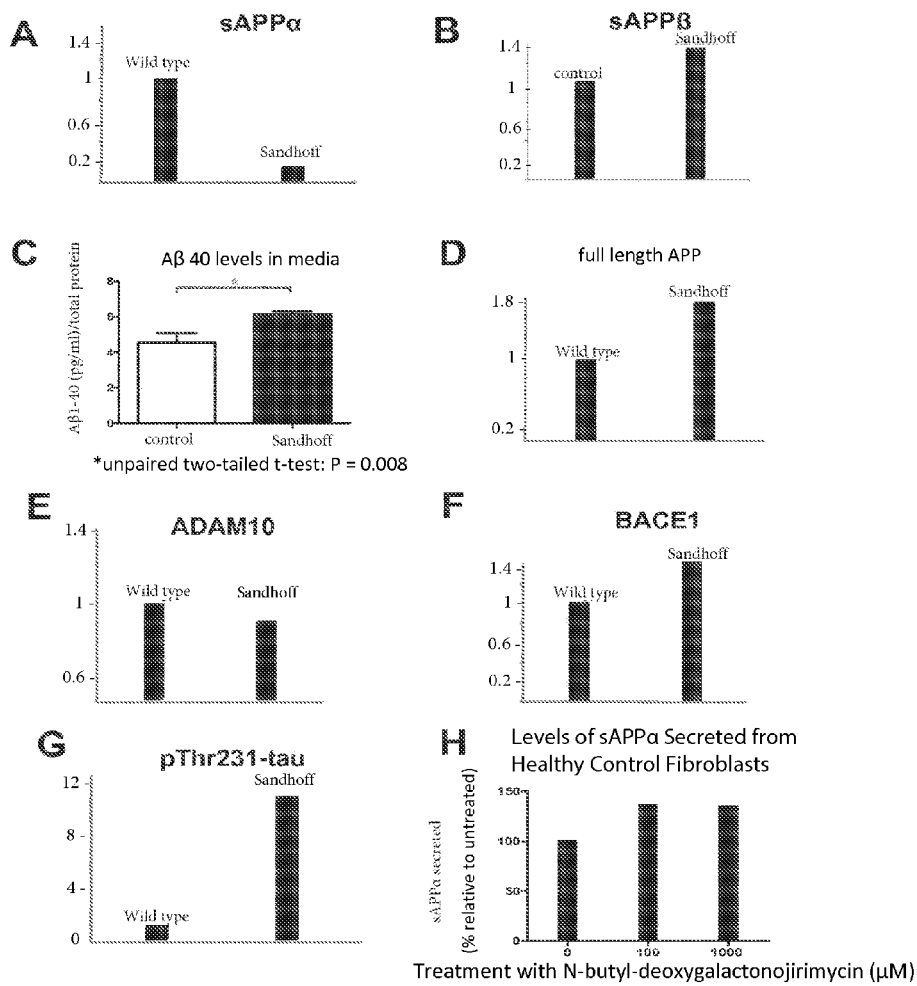
FIG. 3 shows Sandhoff patient-derived fibroblasts secrete more sAPPβ and Aβ and less sAPPα compared to control fibroblasts and exhibit tau hyperphosphorylation.

As shown in FIG. 3, Sandhoff patient-derived fibroblasts secrete more sAPPβ and Aβ and less sAPPα compared to control fibroblasts and exhibit tau hyperphosphorylation. Western blots comparing the levels of sAPPα (A), sAPPβ (B), Aβ (C) ADAM10 (D), BACE1 (E), full length APP (F) and pThr231-tau (G) in fibroblasts derived from healthy controls and a Sandhoff patient using the following antibodies: 6E10 for detection of sAPPα and full length APP; APP(CT) polyclonal (ProSci Inc.) for detection of full length APP; rabbit polyclonal anti-ADAM10 (Calbiochem); rabbit polyclonal anti-BACE1 (Abcam, ab23796); AT180, mAb specific against pThr231-tau (Thermo Scientific); and HT7, mAb specific against human tau (Thermo Scientific). Treatment of Sandhoff fibroblasts (5 days) with the pharmacological chaperone N-butyl-deoxygalactonojirimycin increases the production of sAPPα by 35-40% (H) demonstrating that reducing ganglioside levels can at least partially restore normal APP processing. Sandhoff fibroblasts secreted less sAPPα into the medium compared to control fibroblasts even though ADAM10 and BACE1 levels were similar to controls. Fibroblasts were grown in serum-free DMEM for 20 hours and supernatant Aβ40 concentrations were measured by ELISA (Covance BetaMark x-40) after concentration using C18 Sep-Pak columns (Waters, Inc.). Aβ40 concentrations are normalized to total protein (BCA, Pierce) from fibroblast cell lysates from which the supernatants were derived.

The data shown in FIG. 4 was generated as follows. N2A mouse neuroblastomas were treated for 3 days either with no compound or with 10 μM AdDNJ, 10 μM NGT or 10 μM DGJ. The cells were scraped, harvested by centrifugation, and the cell pellet was solubilized using RIPA buffer (1% TX100, 0.5% Taurodeoxycholate, and 0.1% SDS in TBS plus protease inhibitors). The cell lysate was immunoblotted using a rabbit polyclonal antibody specific for HexB (Abcam). The levels of sAPPα were determined by immunoblotting using a small fraction (30 μl) of the growth media using 22C11 antibody (Millipore).

Figure 4:
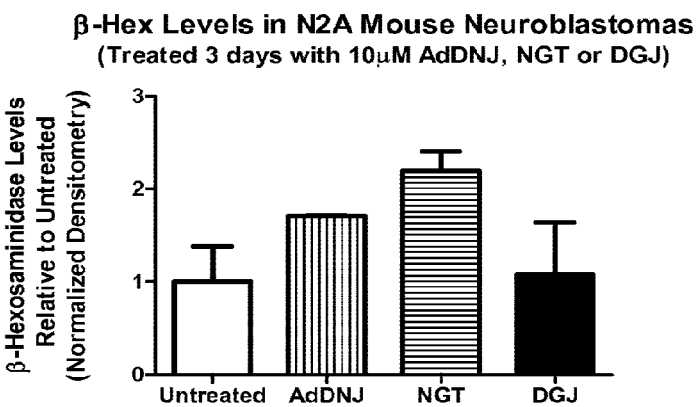
FIG. 4 shows the increase in endogenous wild-type β-hexosaminidase levels and sAPPα shedding in N2A mouse neuroblastomas treated with the pharmacological chaperones NGT and AdDNJ
Figure 4:
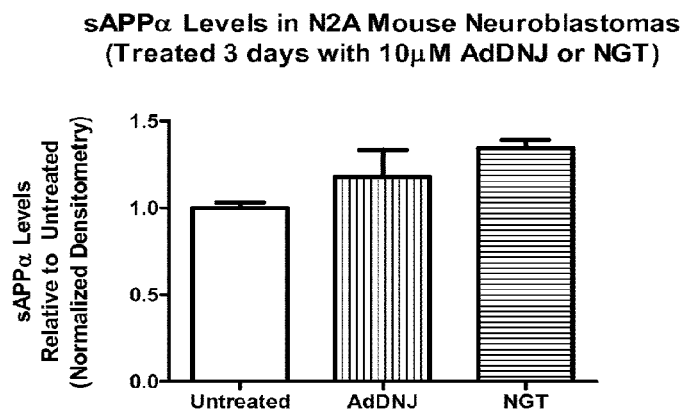

As shown in FIG. 4, β-Hexosaminidase (β-Hex) targeted pharmacological chaperones N-acetyl-glucosamine-thiazoline (NGT) and 2-acetamido-1,2-dideoxynojirimycin (AdDNJ) increase cellular levels of wild-type β-Hex and increase the shedding of neurotrophic sAPPα. FIG. 4A) Treatment of N2A mouse neuroblastomas with 10 μM NGT and AdDNJ increased cellular levels of wild-type β-Hex while deoxygalactonojirimycin (DGJ), a pharmacological chaperone for the lysosomal enzyme acid α-galactosidase, had no effect on β-Hex levels. FIG. 4B) Treatment of N2A mouse neuroblastomas with 10 μM NGT and AdDNJ also increased the shedding of neurotrophic sAPPα.

The data shown in FIG. 5 was generated as follows. For the dose response study, C57BL6 mice were treated with 0, 3 mg/Kg, 10 mg/Kg, 30 mg/Kg, 100 mg/Kg or 300 mg/Kg NGT (drinking water) for 7 days. After dosing, the mice were sacrificed and brain tissue was recovered for enzyme activity measurements. The brain tissue was sliced into 20-30 mg aliquots and each aliquot was homogenized in lysis buffer (82.4 mM Sodium Phosphate dibasic, 58.8 mM Citric acid, 0.25% Taurocholic acid sodium salt hydrate, 0.5% TX-100). The brain tissue homogenate was centrifuged at 25,000 rpm, 4° C. for 15 min. The resulting supernatant (brain lysate) was used for measuring total β-Hexosaminidase activity using the fluorescent substrate 4-Methylumbelliferyl N-acetyl-β-D-glucosaminide (Sigma). For the washout study, C57BL6 mice were treated with 100 mg/Kg NGT (drinking water) for 7 days followed by 1, 2, 3, 5 and 7 days of washout (no drug administered). After the washout phase, the mice were sacrificed and brain tissue was recovered for enzyme activity measurements. The brain tissue was sliced into 20-30 mg aliquots and each aliquot was homogenized in lysis buffer (82.4 mM Sodium Phosphate dibasic, 58.8 mM Citric acid, 0.25% Taurocholic acid sodium salt hydrate, 0.5% TX-100). The brain tissue homogenate was centrifuged at 25,000 rpm, 4° C. for 15 min. The resulting supernatant (brain lysate) was used for measuring total β-Hexosaminidase activity using the fluorescent substrate 4-Methylumbelliferyl N-acetyl-β-D-glucosaminide (Sigma). Brain and plasma levels of NGT were measured by LC-MSMS.

As shown in FIG. 5, the pharmacological chaperone N-acetyl-glucosamine-thiazoline (NGT) selectively increases wild-type endogenous β-hexosaminidase activity in C57BL6 mice. The chaperone N-acetyl-glucosamine-thiazoline is orally available, penetrates the brain, and selectively increases endogenous β-hexosaminidase activity in the brains of C57BL6 mice. NGT treatment (A) demonstrated a dose dependant increase in wild-type β-hexosaminidase activity in the brains of C57BL6 and β-hexosaminidase activity remained elevated (B) above untreated levels for up to 1 week after drug was withdrawn. Plasma (C) and brain levels (D) of N-acetyl-glucosamine-thiazoline after ad lib administration of 3, 10, 30, 100 or 300 mg/kg N-acetyl-glucosamine-thiazoline.

The data shown in FIG. 6 was generated as follows. NGT was administered daily via drinking water at 30 and 100 mg/Kg to wild type C57BL6 mice. Animals were sacrificed on days 2, 4, 6, 8 and 15 (representing 1, 3, 5, 7 and 14 days of dosing respectively). For each time point in this time course experiment, there was also a group of mice that did not receive any NGT (untreated control). After dosing, the mice were sacrificed and brain tissue was recovered for enzyme activity measurements. The brain tissue was sliced into 20-30 mg aliquots and each aliquot was homogenized in lysis buffer (82.4 mM Sodium Phosphate dibasic, 58.8 mM Citric acid, 0.25% Taurocholic acid sodium salt hydrate, 0.5% TX-100). The brain tissue homogenate was centrifuged at 25,000 rpm, 4° C. for 15 min. The resulting supernatant (brain lysate) was used for measuring total β-Hexosaminidase activity using the fluorescent substrate 4-Methylumbelliferyl N-acetyl-β-D-glucosaminide (Sigma). To determine the levels of sAPP in the brain samples from the time course experiment, 40-50 mg of brain tissue was minced and mixed with 10× volume (1 ml/100 mg tissue) of cold tissue homogenization buffer (THB: 250 mM sucrose, 50 mM Tris pH 7.5, 1 mM EDTA plus protease inhibitors). The brain tissue was then homogenized using rotor stator homogenizer. The brain homogenate was transferred into a clean ultra centrifuge tube, placed in a pre-chilled RP70-AT rotor and centrifuged at 50,000 rpm (~100,000 g) for 1 hr at 4° C. The soluble fraction (supernatant) was used for determining the levels of sAPP by immunoblotting using the 22C11 antibody (Millipore).

As shown in FIG. 6, the pharmacological chaperone N-acetyl-glucosamine-thiazoline (NGT) selectively increases wild-type endogenous β-hexosaminidase activity in C57BL6 mice. The chaperone N-acetyl-glucosamine-thiazoline is orally available, penetrates the brain, and selectively increases endogenous β-hexosaminidase activity in the brains of C57BL6 mice. NGT treatment increased wild-type β-hexosaminidase activity (A) and neurotrophic sAPPα levels (B) by nearly 3-fold in the brains of C57BL6 mice within 7 days of treatment. Treatment with NGT had no effect on full length APP levels or gene expression (not shown).

The data shown in FIG. 7 was generated as follows. Healthy control fibroblasts were treated for 5 days either with NB-DANA or IFG. The cells were scraped, harvested by centrifugation, and the cell pellet was solubilized using RIPA buffer (1% TX100, 0.5% Taurodeoxycholate, and 0.1% SDS in TBS plus protease inhibitors). The cell lysate was immunoblotted using a polyclonal antibody specific for Neu1 (Novus).

As shown in FIG. 7, the pharmacological chaperone n-butyl-2-deoxy-2,3-dehydro-N-acetylneuraminic acid (NB-DANA) selectively increases wild-type endogenous neuraminidase-1 levels in fibroblasts derived from healthy individuals. (A) The pharmacological chaperone NB-DANA increased wild-type endogenous neuraminidase 1 levels by up to 2 fold. (B) isofagomine (IFG), a pharmacological chaperone for glucocerebrosidase, does not increase wild-type neuraminidase 1 levels in fibroblasts. Fibroblasts derived from healthy individuals were treated with NB-DANA or IFG for 5 days and enzyme activity was measured in cell lysates using the substrate NANA-4-MU. Enzyme activity was expressed as nmol of 4-MU generated per mg protein per hour.

Figure 8:
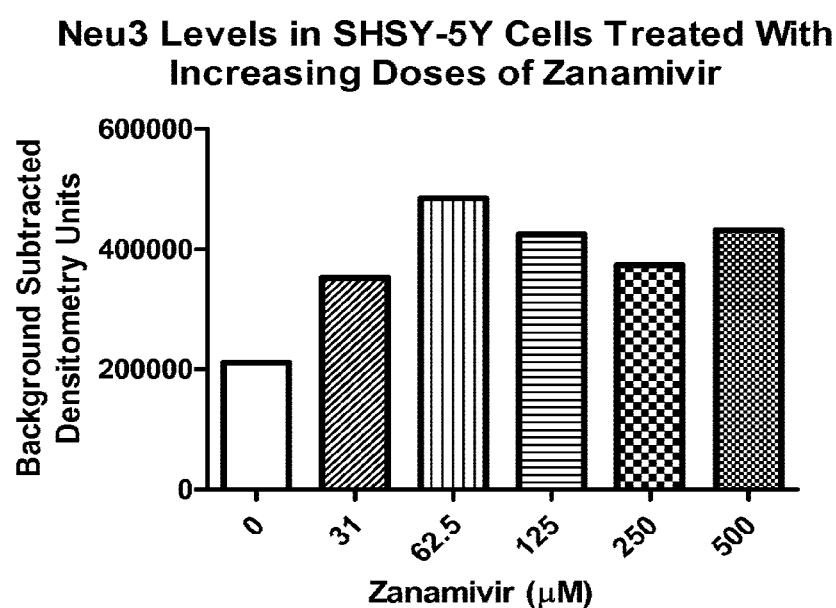
FIG. 8 shows the increase in neuraminidase 3 levels in SHSY-5Y neuroblastomas due to the pharmacological chaperone Zanamivir.

As shown in FIG. 8, the pharmacological chaperone Zanamivir increases wild-type endogenous neuraminidase 3 (Neu3) levels in SHSY-5Y neuroblastoma cells. The data shown in FIG. 8 was generated as follows. SHSY-5Y cells were treated with increasing doses of Zanamivir or vehicle (PBS) as indicated for 72 hours. Cells were harvested after 72 hours of treatment, lysed in TBS+2% CHAPS and insoluble material removed by centrifigation at 40 C (20,000× rpm 10 minutes; eppendorf centrifuge). Supernatants were removed, and protein measured by BCA. Equivalent amounts of protein were loaded onto a 4-12% NuPage gel and resolved by electrophoresis. Proteins were transferred to PVDF membrane and the membrane was probed with a polyclonal antibody to Neu3. Neu3 positive bands were quantified by densitometry. The blot was stripped and re-probed with a monoclonal antibody to tubulin as a protein load control.

What is claimed is:

1. A method for the treatment of Cerebral Amyloid Angiopathy in an individual, comprising administering to the individual an effective amount of a pharmacological chaperone, wherein the pharmacological chaperone is selected from 2-acetamido-1,2-dideoxynojirimycin and N-acetyl-glucosamine-thiazoline.

2. The method of claim 1, wherein the pharmacological chaperone increases production of sAPPα.

3. The method of claim 1, wherein the pharmacological chaperone is 2-acetamido-1,2-dideoxynojirimycin.

4. The method of claim 1, wherein the pharmacological chaperone is N-acetylglucosamine-thiazoline.

5. The method of claim 1, wherein the Cerebral Amyloid Angiopathy is Familial Cerebral Amyloid Angiopathy.

6. The method of claim 5, wherein the Familial Cerebral Amyloid Angiopathy is caused by a mutation in amyloid precursor protein (APP).

* * * * *